(12) United States Patent
Ilg

(10) Patent No.: US 11,932,857 B2
(45) Date of Patent: Mar. 19, 2024

(54) IMMUNOSTIMULATORY OLIGONUCLEOTIDES

(71) Applicant: BAYER ANIMAL HEALTH GMBH, Leverkusen (DE)

(72) Inventor: Thomas Ilg, Monheim (DE)

(73) Assignee: Elanco Animal Health GmbH, Monheim am Rhein (DE)

( * ) Notice: Subject to any disclaimer, the term of this patent is extended or adjusted under 35 U.S.C. 154(b) by 468 days.

(21) Appl. No.: 16/772,541

(22) PCT Filed: Dec. 7, 2018

(86) PCT No.: PCT/EP2018/084019
§ 371 (c)(1),
(2) Date: Jun. 12, 2020

(87) PCT Pub. No.: WO2019/115402
PCT Pub. Date: Jun. 20, 2019

(65) Prior Publication Data
US 2020/0385733 A1      Dec. 10, 2020

(30) Foreign Application Priority Data

Dec. 15, 2017 (EP) .................................. 17207740
Dec. 15, 2017 (EP) .................................. 17207746
Dec. 15, 2017 (EP) .................................. 17207750

(51) Int. Cl.
*C12N 15/117* (2010.01)
*A61K 39/00* (2006.01)
(Continued)

(52) U.S. Cl.
CPC ............ *C12N 15/117* (2013.01); *A61K 39/39* (2013.01); *A61P 37/04* (2018.01);
(Continued)

(58) Field of Classification Search
None
See application file for complete search history.

(56) References Cited

U.S. PATENT DOCUMENTS 5,719,028 A * 2/1998 Dahlberg ............... C07H 21/00
435/5
7,271,156 B2 9/2007 Krieg et al.
(Continued)

FOREIGN PATENT DOCUMENTS

CN        1637013 C    7/2005
CN      104718221 B    6/2015
(Continued)

OTHER PUBLICATIONS

Spiller et al. Improving the intracellular delivery and molecular efficacy of antisense oligonucleotides in chronic myeloid leukemia cells: a comparison of streptolysin-O permeabilization, electroporation, and lipophilic conjugation. Blood. Jun. 15, 1998;91(12):473 (Year: 1998).*

(Continued)

*Primary Examiner* — Michelle S Horning
(74) *Attorney, Agent, or Firm* — McBee Moore & Vanik IP, LLC; Susan E. Shaw McBee; Christopher Nichols

(57) ABSTRACT

Compositions and methods for stimulating toll-like receptor 9 (TLR9) are provided. More particularly, immunostimulatory oligonucleotides, methods of enhancing immunostimulatory properties of oligonucleotides, and methods of eliciting immune responses are disclosed herein.

42 Claims, 19 Drawing Sheets
Specification includes a Sequence Listing.

(51) Int. Cl.
*A61K 39/39* (2006.01)
*A61P 37/04* (2006.01)

(52) U.S. Cl.
CPC .............. *A61K 2039/55555* (2013.01); *A61K 2039/55561* (2013.01); *A61K 2039/60* (2013.01); *C12N 2310/17* (2013.01); *C12N 2310/315* (2013.01); *C12N 2310/3341* (2013.01); *C12N 2310/3515* (2013.01); *C12N 2320/31* (2013.01)

(56) References Cited

U.S. PATENT DOCUMENTS

| | | | |
|---|---|---|---|
| 7,408,050 B2 * | 8/2008 | Kim | A61P 1/16 424/278.1 |
| 7,615,539 B2 | 11/2009 | Uhlmann et al. | |
| 8,128,944 B2 | 3/2012 | Jurk et al. | |
| 8,283,328 B2 | 10/2012 | Krieg et al. | |
| 9,012,225 B2 | 4/2015 | Vagle et al. | |
| 9,506,030 B2 | 11/2016 | Bhat | |
| 10,029,016 B2 | 7/2018 | Irvine et al. | |
| 10,112,985 B2 | 10/2018 | Ilg et al. | |
| 10,456,463 B2 | 10/2019 | Davis et al. | |
| 2003/0212026 A1 * | 11/2003 | Krieg | A61P 37/04 514/44 R |
| 2005/0130911 A1 | 6/2005 | Uhlmann et al. | |
| 2008/0045473 A1 | 2/2008 | Uhlmann et al. | |
| 2008/0124366 A1 | 5/2008 | Ohlfest et al. | |
| 2016/0289761 A1 * | 10/2016 | French | C12Q 1/6883 |

FOREIGN PATENT DOCUMENTS

| | | |
|---|---|---|
| JP | 2003-510282 A | 3/2003 |
| JP | 2005-192552 A | 7/2005 |
| JP | 2006-508693 A | 3/2006 |
| JP | 2007-506790 A | 3/2007 |
| JP | 2009-528027 A2 | 8/2009 |
| JP | 2010-536739 A | 12/2010 |
| JP | 2011-251963 A | 12/2011 |
| JP | 2012-526132 A | 10/2012 |
| JP | 2015-514108 A | 5/2015 |
| JP | 2015-522266 A | 8/2015 |
| JP | 2016-518841 A | 6/2016 |
| TW | 200916106 A | 4/2009 |
| TW | 201505657 A | 2/2015 |
| WO | 2004/016805 | 2/2004 |
| WO | 2004/016805 A2 | 2/2004 |
| WO | 2005/30259 A2 | 4/2005 |
| WO | 2007/95316 A2 | 8/2007 |
| WO | 2008/068638 | 6/2008 |
| WO | 2009/022216 A2 | 2/2009 |
| WO | 2010/129672 A1 | 11/2010 |
| WO | 2014/179445 A1 | 11/2014 |
| WO | 2015/010070 A1 | 1/2015 |

OTHER PUBLICATIONS

Kawasaki T, Kawai T. Toll-like receptor signaling pathways. Front Immunol. Sep. 25, 2014;5:461. (Year: 2014).*

Uhlmann, Eugen et al., "Recent advances in the development of immunostimulatory oligonucleotides", Current Opinion in Drug Discovery and Development, Jan. 1, 2003, pp. 204-217, vol. 6, No. 2.

International Search Report of International Patent Application No. PCT/EP2018/084019 dated Feb. 25, 2019.

Uhlmann Eugen et al: "Recent advances in the development of immunostimulatory oligonucleotides.", Current Opinion in Drug Discovery & Development Mar. 2003, Mar. 2003 (Mar. 1, 2003), pp. 204-217, vol. 6, No. 2, XP009103505.

Peel et al., "Conjugation and evaluation of Small Hudrophobic Molecules to Trialoze-Linked siRNAs", Med. Chem. Lett., 2015, vol. 6, pp. 117-122.

"Spacer modified oligo DNA", [online], Sep. 23, 2017, http://ngrl.co.jp/wp/wp-content/uploads/2014/08/260d341b509ecb2a938d6259c3e32552.pdf.

* cited by examiner

SEQUENCE LISTING

<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: Synthetic Oligonucleotide 2006-PTO

<400> SEQUENCE: 1
tcgtcgtttt gtcgttttgt cgtt                                          24

<210> SEQ ID NO 2
<211> LENGTH: 37
<212> TYPE: DNA
<213> ORGANISM: Artificial Sequence
<220> FEATURE:
<223> OTHER INFORMATION: Synthetic Oligonucleotide 2006-3dT4G5T4

<400> SEQUENCE: 2
tcgtcgtttt gtcgttttgt cgttttttgg gggtttt                            37

<210> SEQ ID NO 3
<211> LENGTH: 28
<212> TYPE: DNA
<213> ORGANISM: Artificial Sequence
<220> FEATURE:
<223> OTHER INFORMATION: Synthetic Oligonucleotide 2006-T4-PDE

<400> SEQUENCE: 3
tcgtcgtttt gtcgttttgt cgttttttt                                     28

<210> SEQ ID NO 4
<211> LENGTH: 26
<212> TYPE: DNA
<213> ORGANISM: Artificial Sequence
<220> FEATURE:
<223> OTHER INFORMATION: Synthetic Oligonucleotide 2007-PDE-T4

<400> SEQUENCE: 4
tcgtcgttgt cgttttgtcg tttttt                                        26

<210> SEQ ID NO 5
<211> LENGTH: 35
<212> TYPE: DNA

```
<213> ORGANISM: Artificial Sequence
<220> FEATURE:
<223> OTHER INFORMATION: Synthetic Oligonucleotide 2007-T4G5T4

<400> SEQUENCE: 5
tcgtcgttgt cgttttgtcg tttttggggg gtttt                              35

<210> SEQ ID NO 6
<211> LENGTH: 28
<212> TYPE: DNA
<213> ORGANISM: Artificial Sequence
<220> FEATURE:
<223> OTHER INFORMATION: Synthetic Oligonucleotide TCG8-T4

<400> SEQUENCE: 6
tcgtcgtcgt cgtcgtcgtc gtcgtttt                                      28

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide 2006-G5

<400> SEQUENCE: 7
tcgtcgtttt gtcgttttgt cgttggggg                                     29

<210> SEQ ID NO 8
<211> LENGTH: 37
<212> TYPE: DNA
<213> ORGANISM: Artificial Sequence
<220> FEATURE:
<223> OTHER INFORMATION: Synthetic Oligonucleotide TCG8-T4G5T4

<400> SEQUENCE: 8
tcgtcgtcgt cgtcgtcgtc gtcgttttgg gggtttt                            37

<210> SEQ ID NO 9
<211> LENGTH: 13
<212> TYPE: DNA
<213> ORGANISM: Artificial Sequence
<220> FEATURE:
<223> OTHER INFORMATION: Synthetic Oligonucleotide PDE-2006

<400> SEQUENCE: 9
ttttgggggt ttt                                                      13
```

IMMUNOSTIMULATORY OLIGONUCLEOTIDES

CROSS-REFERENCE TO RELATED APPLICATIONS

This application is a National Stage entry of International Application No. PCT/EP2018/084019, filed 7 Dec. 2018, which claims priority to European Patent Application Nos. 17207740.6, filed 15 Dec. 2017, 17207746.3, filed 15 Dec. 2017, and 17207750.5, filed 15 Dec. 2017.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence Listing 2920493-032000 ST25.txt" created on 15 May 2020, and 2,246 bytes in size) is submitted concurrently with the instant application, and the entire contents of the Sequence Listing are incorporated herein by reference.

BACKGROUND

Field

Compositions and methods for stimulating toll-like receptor 9 (TLR9) are provided. More particularly, immunostimulatory oligonucleotides, methods of enhancing immunostimulatory properties of oligonucleotides, and methods of eliciting immune responses are disclosed herein.

Description of Related Art

Antibiotic resistance is a global problem negatively affecting numerous industries. Methicillin resistant *Staphylococcus aureus* (MRSA) and other "super bugs" are creating havoc in hospitals and doctors' offices, making visits to health centers potentially lethal. The agriculture industry sees similar issues. Entire herds are at risk of pathogenic infection due to limited space and non-sterile environments. One sick cow, for example, in close proximity to her herd can exponentially increase morbidity and mortality rates. Despite the risk of infections, antibiotic treatments are becoming more disfavored due to increased costs and consumers demanding meats and dairy products that have not been exposed to antibiotics. And those producers who do use antibiotic therapies understand that even broad spectrum antibiotics are not entirely effective against every pathogen that may come in contact with a herd.

Thus, there is a need for non-antibiotic based therapies for treating or preventing infection in animals. The disclosed compositions and methods are directed to these and other important needs.

SUMMARY

Disclosed herein are immunostimulatory oligonucleotides comprising at least one CpG motif and a 3' cholesteryl moiety.

Immunostimulatory compositions comprising immunostimulatory oligonucleotides are also provided herein.

Also disclosed are methods for enhancing the immunogenicity of a TLR9 ligand comprising attaching a cholesteryl moiety to the 3' terminus of the TLR9 ligand via a linker, wherein the TLR9 ligand is an oligonucleotide having at least one CpG motif.

Methods are also provided for eliciting a TLR9-mediated immune response in a subject comprising administering to the subject any one of the immunostimulatory oligonucleotides or the immunostimulatory compositions described herein.

BRIEF DESCRIPTION OF THE DRAWINGS

The summary, as well as the following detailed description, is further understood when read in conjunction with the appended drawings. For the purpose of illustrating the disclosed compositions and methods, there are shown in the drawings exemplary embodiments of the compositions and methods; however, the compositions and methods are not limited to the specific embodiments disclosed. In the drawings:

FIG. 8A compares the ability of oligonucleotide 2007-PDE-T4oligonucleotide to elicit a TLR9-mediated immune response in HEKBlue-hTLR9 cells to that of oligonucleotide 2007-PDE-T4 oligonucleotide with a cholesteryl moiety attached via a hexanediol linker of FIG. 1 ("2007-PDE-T4-3Ch"), and FIG. 8B compares the ability of oligonucleotide 2007-PDE-T4 having a 3' GGGGGTTTT sequence ("2007-T4G5T4"), and oligonucleotide 2007-T4G5T4 with a cholesteryl moiety attached via a hexanediol linker shown in FIG. 1 ("2007-T4G5T4-3Ch") in HEKBlue-hTLR9 cells.

FIG. 9A illustrates the immunogenicity of 2006-PTO, 2006-3dT4G5T4, and 2006-3dT4G5T4C oligonucleotides via a TLR9-mediated immune response in Ramos-Blue cells, and FIG. 9B illustrates the results depicted in FIG. 9A over narrower concentration range.

FIG. 10A illustrates the relative ability of oligonucleotides 2006-3dT4G5T4 and 2006-3dT4G5T4C to elicit a TLR9-mediated immune response. FIG. 10B illustrates the results of FIG. 10A over a narrower concentration range.

FIG. 13A illustrates the different immunogenicities of oligonucleotides 2007-PDE-T4 and 2007-PDE-T4-Ch3. FIG. 13B illustrates the different immunogenicities of oligonucleotides 2007-T4G5T4 and 2007-T4G5T4-3Ch. FIG. 13C illustrates the different immunogenicities of oligonucleotides TCG8-T4 and TCG8-T4-Ch3.

FIG. 14A compares the ability to elicit a TLR9-mediated response in HEKBlue-mTLR9 cells of an unmodified 2007-PDE-T4 oligonucleotide and oligonucleotide 2007-PDE-T4-3Ch. FIG. 14B compares the ability of an unmodified 2007-T4G5T4 oligonucleotide and oligonucleotide 2007-T4G5T4-3Ch to elicit a TLR9-mediated response in HEKBlue-mTLR9 cells. FIG. 14C compares the ability of oligonucleotide TCG8-T4 and oligonucleotide TCG8-T4-3Ch to elicit a TLR9-mediated response in HEKBlue-mTLR9 cells; and FIG. 14D compares the ability of TCG8-T4G5T4 oligonucleotide and oligonucleotide TCG8-T4G5T4 having a 3' cholesteryl moiety attached via a hexanediol linker shown in FIG. 1 ("TCG8-T4G5T4-3Ch") to elicit a TLR9-mediated response in HEKBlue-mTLR9 cells.

FIG. 16A graphically depicts the ability to stimulate TLR9 in HEKBlue-hTLR9 cells of oligonucleotides 2006-PDE-T4, 2006-PDE-T4-Chol, and oligonucleotide 2006-PDE-T4 having a 5' cholesteryl moiety attached via a hexaethylene glycol linker shown in FIG. 15 ("2006-PDE-T4-5Chol"). FIG. 16B graphically depicts the ability to stimulate TLR9 in HEK-Blue-hTLR9 cells of oligonucleotide 2006-PTO, oligonucleotide 2006-PDE having a GGGGG 3' terminal sequence ("2006-G5"), oligonucleotide 2006-G5 having a 3' cholesteryl moiety attached via a hexaethylene glycol linker shown in FIG. 6 ("2006-G5-3Chol"), and oligonucleotide 2006-G5 having a 5' cholesteryl moiety attached via a hexaethylene glycol linker shown in FIG. 15 ("2006-G5-5Chol"). FIG. 16C graphically depicts the ability to stimulate TLR9-mediated immune responses in HEKBlue-hTLR9 cells of oligonucleotides 2006-PTO, 2006-T4G5T4, 2006-T4G5T4-3Chol, and oligonucleotide 2006-T4G5T4 having a 5' cholesteryl moiety attached via a hexaethylene glycol linker shown in FIG. 15 ("2006-T4G5T4-5Chol"). FIG. 16D graphically depicts the ability to stimulate TLR9-mediated immune responses in HEKBlue-hTLR9 cells of oligonucleotide TCG8-T4G5T4, oligonucleotide TCG8-T4G5T4 having a 3' cholesteryl moiety attached via a hexaethylene glycol linker shown in FIG. 6 ("TCG8-T4G5T4-3Chol"), and oligonucleotide TCG8-T4G5T4 having a 5' cholesteryl moiety attached via a hexaethylene glycol linker shown in FIG. 15 ("TCG8-T4G5T4-5Chol").

FIG. 17A graphically depicts the ability to stimulate TLR9 in Ramos-Blue cells of oligonucleotides 2006-PDE-T4, 2006-PDE-T4-Chol, and 2006-PDE-T4-5Chol. FIG. 17B graphically depicts the ability to stimulate TLR9 in Ramos-Blue cells of oligonucleotide 2006-PTO, 2006-G5, 2006-G5-3Chol, and 2006-G5-5Chol. FIG. 17C graphically depicts the ability to stimulate TLR9-mediated immune responses in Ramos-Blue cells of oligonucleotides 2006-PTO, 2006-T4G5T4, 2006-T4G5T4-3Chol, and oligonucleotide 2006-T4G5T4-5Chol. FIG. 17D graphically depicts the ability to stimulate TLR9-mediated immune responses in Ramos-Blue cells of oligonucleotides TCG8-T4G5T4, TCG8-T4G5T4-3Chol, and TCG8-T4G5T4-5Chol.

DETAILED DESCRIPTION OF A PREFERRED EMBODIMENT

Figure 1:
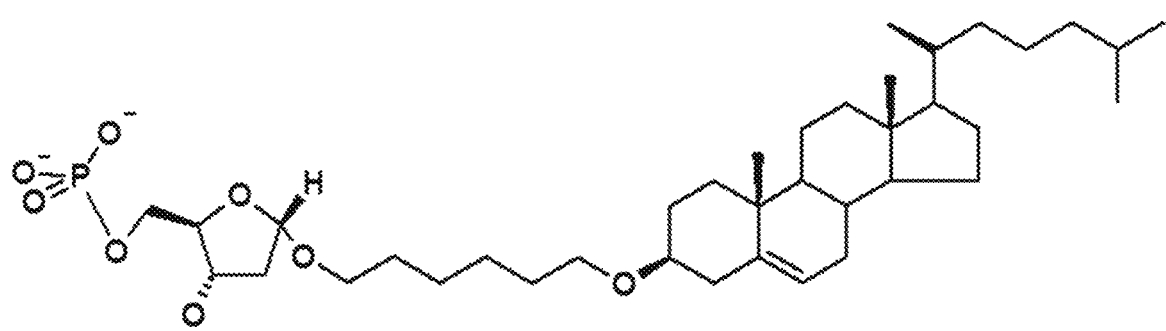
FIG. 1 depicts the chemical structure of a cholesteryl moiety attached to a hexanediol linker.

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Unless specifically stated otherwise, any description as to a possible mechanism or mode of action or reason for improvement is meant to be illustrative only, and the disclosed compositions and methods are not to be constrained by the correctness or incorrectness of any such suggested mechanism or mode of action or reason for improvement.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

When a range of values is expressed, another embodiment includes from the one particular value and/or to the other particular value. Further, reference to values stated in ranges includes each and every value within that range. All ranges are inclusive and combinable. When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

As used herein, the singular forms "a," "an," and "the" include the plural.

As used herein, "CpG motif" refers to a cytosine-guanine dinucleotide sequence. The immunostimulatory nucleic acids described herein contain one or more CpG motifs, which when unmethylated can interact with toll-like receptor proteins (TLRs) and elicit an immune response.

The term "subject" as used herein is intended to mean any animal, in particular, mammals, and any type of avian, mammalian, or aquatic species can be treated using the disclosed methods.

Various terms relating to aspects of the description are used throughout the specification and claims. Such terms are to be given their ordinary meaning in the art unless otherwise indicated. Other specifically defined terms are to be construed in a manner consistent with the definitions provided herein.

Disclosed herein are immunostimulatory oligonucleotides comprising at least one CpG motif and a 3'-terminal cholesteryl moiety. It has been previously shown that CpG motifs in oligodeoxynucleotides (ODN) can elicit an immune response in mammals. In some instances, the CpG motif is recognized by a toll-like receptor (TLR). Examples of CpG-recognizing TLRs include, but are not limited to, mammalian homologs of TLR9. Thus in some aspects of the present disclosures, the CpG-recognizing TLR is a mouse, human, cow, pig, horse, or sheep TLR9 homolog. The immunogenicity of an ODN may not be sufficient to elicit immune responses capable of warding off infection in susceptible populations or infected individuals. As demonstrated herein, the immunostimulatory properties of an ODN can be enhanced by modifying oligonucleotides, especially with the addition of a thymine run, a guanine run, and/or a cholesteryl moiety at the 3' terminus of the ODN.

The immunostimulatory oligonucleotides of the present disclosure comprise at least one CpG motif. In some embodiments, the immunostimulatory oligonucleotides comprise between one and ten CpG motifs. In other embodiments the immunostimulatory oligonucleotides can comprise even twenty CpG motifs. Thus, in some embodiments, the immunostimulatory oligonucleotides of the present disclosure comprise one, two, three, four, five, six, seven, eight, nine, or ten CpG motifs. In other embodiments, the immunostimulatory oligonucleotides comprise between eleven and fifteen CpG motifs or even between fifteen and twenty CpG motifs.

Oligonucleotides comprising phosphodiester and/or phosphorothioate linkages between nucleotides are contemplated herein. In some aspects, the oligonucleotides of the present disclosure comprise phosphodiester linkages between the oligonucleotide's nucleotides. In other aspects, the oligonucleotides comprise phosphorothioate linkages between the oligonucleotide's nucleotides. Other linkages are also contemplated herein. For example, the oligonucleotide of the present disclosure may comprise other linkages including, but not limited to, phosphoacetate, methylphosphonate, and phosphonocarboxylate linkages. Some of the linkages may provide desirable advantages over the other linkages, such as cost of production, ease and/or quality of production, and enhanced immunostimulatory impact.

In some aspects of the present disclosure, the oligonucleotide's immunogenicity due to the CpG motifs may be further enhanced by non-CpG sequences. As shown in the Examples, the addition of a thymine run to the 3' terminus of the oligonucleotide can improve the ability of the oligonucleotide to elicit a TLR9-mediated immune response. For this reason, in some embodiments of the present disclosures the 3' terminal sequence of the immunostimulatory oligonucleotide comprises a plurality of thymine nucleotides as the 3' terminal sequence. In some aspects, this plurality of thymine nucleotide comprises consecutive thymine nucleotides. In some aspects, the plurality of thymine nucleotides comprises between four and six consecutive thymine nucleotides. For example, in some embodiments of the present disclosure, the 3' terminal sequence comprises SEQ ID NO:9. In some embodiments, the oligonucleotide comprises SEQ ID NO: 2, 3, 4, 5, 6, or 8. And in some aspects, the 3' terminal sequence of the oligonucleotide sequence is TTTT.

Other sequence modifications to the 3' end of the immunostimulatory oligonucleotide may also contribute to enhanced immunogenicity. For example, in some embodiments of the present disclosures, the immunostimulatory oligonucleotide comprises a plurality of guanine nucleotides at or near the 3' terminal sequence. In some aspects, the 3' terminal sequence of the immunostimulatory oligonucleotide comprises a plurality of guanine nucleotides. In some aspects, the plurality of guanine nucleotides comprises consecutive guanine nucleotides, such as an oligonucleotide according to the present disclosure having a 3' terminal sequence of GGGGG. In some aspects, the oligonucleotide comprises SEQ ID NO:7.

Increasing immunogenicity of an immunostimulatory oligonucleotide is not limited to modifications of the 3' terminus of the oligonucleotide. Internal sequences can also be modified, for example, to increase the number of CpG motifs. In some aspects, oligonucleotides can be synthesized comprising additional CpG motifs between the 5' and 3' ends of the oligonucleotide. In some aspects, the immunostimulatory oligonucleotide comprises the sequence $(TCG)_n$, where n is between three and ten. Thus, in some aspects of the present disclosure, the oligonucleotide comprises the sequence $(TCG)_n$, where n is 3, 4, 5, 6, 7, 8, 9, or 10.

In some embodiments of the present disclosure, the immunostimulatory oligonucleotide may comprise a lipid moiety at the 3' terminus to enhance the immunogenic properties of the oligonucleotide. Thus, in some embodiments, a cholesteryl moiety is covalently attached to the 3'-terminal nucleotide of the immunostimulatory oligonucleotide via a linker. The cholesteryl moiety likely increases the oligonucleotide's immunogenicity by preventing degradation, increasing solubility, generating ligand multivalency by forming higher order structures (e.g., micelles), increasing the stability of the oligonucleotide in a pharmaceutical composition, or any combination thereof. The linker, having at least two moieties capable of forming covalent bonds, can bond with the cholesteryl moiety and with the oligonucleotide. For example, in some embodiments the linker interacts with the cholesteryl moiety's hydroxyl group to form a covalent bond and with the 3' terminal nucleotide of an oligonucleotide. In some aspects, the cholesteryl moiety is covalently bound to the linker to form a cholesteryl-linker moiety. In some aspects, the linker is first attached to the cholesteryl moiety and the resulting cholesteryl-linker is then attached to the oligonucleotide. In other aspects, the linker is first attached to the oligonucleotide and then to the cholesteryl moiety. In some aspects, the cholesteryl-linker is commercially available.

Figure 6:
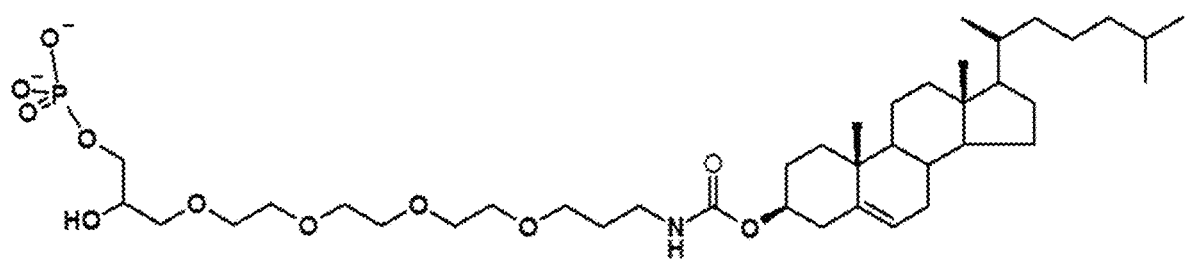
FIG. 6 depicts the chemical structure of a cholesteryl moiety attached to a hexaethylene glycol linker.

In addition to having moieties that can bind to the oligonucleotide and the cholesteryl moiety, some embodiments of the linker comprise a carbon chain, and in some aspects the carbon chain comprises between 3 and 12 carbon atoms. Diols, for example, can be used as a linker between the cholesteryl moiety and the oligonucleotide as the terminal hydroxyl groups can covalently bond with the oligonucleotide's and the cholesteryl moiety's hydroxyl groups. In some aspects, the linker comprises a hexanediol. In some aspects, a cholesteryl-linker moiety has the chemical structure depicted in FIG. 1. Other embodiments provide for a linker comprising a repeated chemical unit. The chemical unit, in some aspects, is repeated between two and twelve times. In some aspects the repeated chemical unit comprises ethylene glycol, and when the ethylene glycol chemical unit is repeated six times, the linker comprises a hexaethylene glycol. A linker comprising hexaethylene glycol may have the chemical structure depicted in FIG. 6.

In some circumstances it will be desirable to deliver an oligonucleotide as described herein to a subject in need thereof. The oligonucleotide may be delivered as an immunostimulatory composition. Immunostimulatory compositions comprising any of the oligonucleotides disclosed herein are provided. These immunostimulatory compositions, in some aspects, comprise the oligonucleotide as well as other components that affect the immunogenicity, effectiveness, and efficiency of the composition. In some embodiments of the present disclosure the immunostimulatory composition may include in addition to the immunostimulatory oligonucleotide a vaccine for preventing or treating an infectious disease, a vector for delivering the oligonucleotide to the subject, a pharmaceutical carrier, or any combination thereof. For example, in some aspects the oligonucleotide is packaged in a viral vector that allows for the targeted delivery of the oligonucleotide. The oligonucleotide may, in some aspects, be added to a cationic liposomal delivery vehicle to enhance the ability of the oligonucleotide to traverse lipid cell membranes and/or membranes of cellular organelles containing TLR9.

Infectious diseases that may be treated or prevented by administration of the immunostimulatory oligonucleotides or immunostimulatory compositions described herein include, but are not limited to, viral, bacterial, fungal, helminthic, or other parasitic infection. It is contemplated that administering the immunostimulatory oligonucleotides or compositions of the present disclosure results in an immune response that creates an environment hostile to an invading pathogen. Therefore, invading pathogens may be unable to establish an infection sufficient to result in a negatively altered health state in the host organism. The administration of the immunostimulatory oligonucleotides and/or compositions may provide a non-antigen-specific immune response that augments or works in parallel with an antigen-specific immune response against an invading pathogen.

In some aspects, the immunostimulatory composition comprising the oligonucleotide may further comprise a vaccine for preventing or treating an infectious disease. The combination of the oligonucleotide and the vaccine may be done for efficiency reasons as delivering multiple pharmaceuticals separately adds to the cost of treatment. The oligonucleotide and the vaccine may also be delivered as a single immunostimulatory composition to elicit a non-antigen specific immune response against any current infections as well as to initiate the development of an antigen specific immune response.

Also contemplated herein are immunostimulatory compositions that comprise an oligonucleotide as described herein and a pharmaceutically acceptable carrier. In some aspects, the pharmaceutically acceptable carrier is any pharmaceutically acceptable carrier. The pharmaceutically acceptable carrier adapts the composition for administration by a route selected from intravenous, intramuscular, intramammary, intradermal, intraperitoneal, subcutaneous, by spray, by aerosol, in ovo, mucosal, transdermal, by immersion, oral, intraocular, intratracheal, intranasal, pulmonary, rectal, or other means known to those skilled in the art. The pharmaceutically acceptable carrier(s) may be a diluent, adjuvant, excipient, or vehicle with which the immunostimulatory composition is administered. Such vehicles may be liquids, such as water and oils, including those of petroleum, animal, vegetable, or synthetic origin, such as peanut oil, soybean oil, mineral oil, sesame oil, and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating, and coloring agents, etc. The concentration of the molecules of the invention in such pharmaceutical formulation may vary widely, i.e., from less than about 0.5%, usually to at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g., Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092 (see especially pp. 958-989).

In some embodiments, the oligonucleotide and the carrier are coupled, e.g., chemically coupled. As used to describe the relationship between the oligonucleotide and the carrier, "coupled" refers to physical association of the oligonucleotide and the carrier. When the oligonucleotide and the carrier are bound to each other, interact with each other, or are combined, or otherwise joined, they can be deemed to be coupled.

The immunostimulatory compositions described herein further comprise a hapten in some embodiments. In some aspects, the immunostimulatory oligonucleotide is linked to the hapten. The hapten may elicit an immunoresponse against a specific microorganism, such as *E. coli* or *Salmonella*, while the immunostimulatory oligonucleotide elicits a non-specific immunoresponse mediated by TLR9 interaction with the oligonucleotide. These and other infectious microorganisms are of particular interest to large agricultural producers, such as cattle, sheep, and pig producers.

Methods are also provided for enhancing the immunogenicity of a TLR9 ligand comprising attaching a cholesteryl moiety to the ligand, wherein the ligand is an immunostimulatory oligonucleotide having at least one CpG motif and wherein the cholesteryl moiety is attached, via a linker, to the 3' terminal nucleotide of the oligonucleotide.

Other methods disclosed herein provide for eliciting a TLR9-mediated immune response in a subject in need thereof comprising administering to the subject an oligonucleotide having a plurality of CpG motifs and a cholesteryl-linker moiety attached to the 3' terminal nucleotide of the oligonucleotide. In some aspects of the methods for eliciting a TLR9-mediated immune response, the oligonucleotide is administered as an immunostimulatory composition.

The subject to which the immunostimulatory oligonucleotide or immunostimulatory composition is administered, in some embodiments of this disclosure, is an animal. In some aspects, the animal is at a heightened risk of infection by a pathogen and especially a pathogen having a CpG-based pathogen associated molecular pattern (PAMP). When an immunostimulatory oligonucleotide and/or immunostimulatory composition is administered to such an animal, a TLR9-mediated immune response will assist in preventing infection by the pathogen or alleviation of symptoms caused by the pathogen. It will be understood by those skilled in the art that the immunostimulatory oligonucleotides of the present invention need not be specific for a particular pathogen, but rather, stimulate a non-antigen specific immune response. The oligonucleotides also need not be specific for a particular animal. Thus, in some aspects of the present disclosure, the subject is a mammal. In some aspects the subject is a herd or farm animal such as a pig, cow, horse or sheep. Administration to herd animals may help prevent the spread of infection to large populations of animals in crowded conditions such as pens and/or sharing common feed or water sources. The oligonucleotides of the present disclosure provide a distinct advantage over traditional forms of prophylactic treatment of infection in that the use of antibiotics is growing more disfavored, especially with the emergence of bacterial resistance to antibiotic therapy.

In some embodiments, the subject may be a human. As with herd animals, resistance to antibiotics consumed by humans is becoming common in bacteria, and treatment options for resistant infections are limited. The oligonucleotides and methods of the present disclosure provide a much needed solution to so-called "super-bugs" such as methicillin-resistant *Staphylococcus aureus*.

It is also contemplated herein that the subject to which the immunostimulatory oligonucleotide or composition is administered to may be a mouse, rat, hamster, gerbil, or other rodent. The subject may also be nonmammalian. For example, the subject, in some aspects, is an aquatic species.

EXAMPLES

The following examples are provided to further describe some of the embodiments disclosed herein. The examples are intended to illustrate, not to limit, the disclosed embodiments.

Example 1: 3'-Cholesteryl Modification of ODNs Results in Strongly Increased TLR9 Stimulatory Activity Human TLR9, Recombinant Overexpression in HEKBlue 3'-Cholesteryl Modification of PDE-ODNs (I)

3'-cholesteryl modification (see FIG. 1 for chemical structure of the cholesteryl-linker moiety) was applied to a PDE-ODN (Table 1, 2006-3dT4G5T4) that has fair activity on human TLR9. The modified and unmodified forms were tested in vitro in HEKBlue-hTLR9 cells (Invivogen), a cell line expressing a human TLR9.

TABLE 1

ODN sequences (lower case: PTO bonds)

| ODN | SEQ ID NO | Sequence |
|---|---|---|
| 2006-PTO | SEQ ID NO: 1 | tcgtcgttttgt cgttttgtcgtt |
| 2006-3dT4G5T4 | SEQ ID NO: 2 | TCGTCGTTTTGTCGTTTG TCGTTTTTTGGGGGTTTT |
| 2006-3dT4G5T43C | SEQ ID NO: 2 | TCGTCGTTTTGTCGTTTG TCGTTTTTTGGGGGTTTTX |

X = 3'-Cholesteryl

TABLE 2

Half maximal effective concentration ($EC_{50}$) and maximum signal velocity ($V_{max}$)

| ODN | $EC_{50}$ nanomolar (nM) | Vmax milliOD 405 nm/min (mOD405/min) |
|---|---|---|
| 2006-PTO | 26.0 | 56 |
| 2006-3dT4G5T4 | 404 | 120 |
| 2006-3dT4G5T43C | 13.6 | 103 |

Figure 2A:
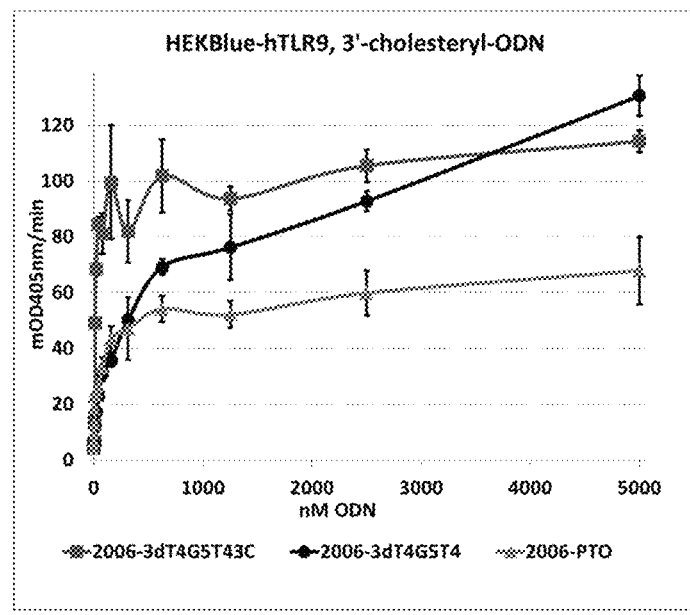
FIGS. 2A and 2B compare the TLR9 stimulatory activity of oligonucleotide PTO-2006, oligonucleotide PDE-2006 having a 3' TTTTGGGGGTTTT (SEQ ID NO:9) sequence ("2006-3dT4G5T4"), and oligonucleotide 2006-3dT4G5T4 having a 3' cholesteryl moiety attached via a hexanediol linker shown in FIG. 1 ("2006-3dT4G5T43C") in HEK-Blue-hTLR9 cells.
Figure 2B:
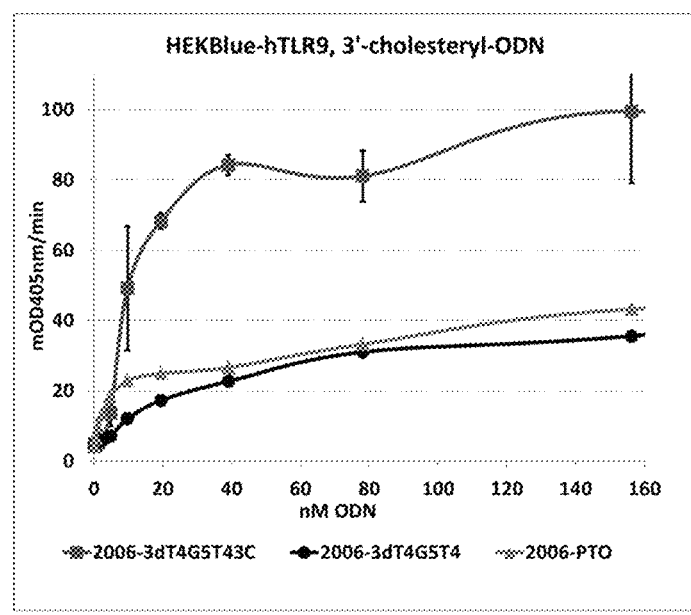

The results suggest that the TLR9-stimulatory activity of 2006-3dT4G5T4 improves considerably upon 3'-cholesteryl modification with respect to the $EC_{50}$, which is almost 30-fold lower for 2006-3dT4G5T43C (Table 2, FIGS. 2A, 2B).

3'-Cholesteryl Modification of PDE-ODNs (II)

A cholesteryl moiety (see FIG. 1 for the chemical structure of the cholesteryl-linker moiety) was attached to the 3' terminal nucleotide of 2006-T4-PDE (SEQ ID NO:3, Table 3) that is known to be a poor activating ligand of human TLR9. The modified and unmodified 2006-T4-PDE oligonucleotides were administered in vitro to HEKBlue-hTLR9 cells to determine the immunostimulatory impact of the 3'-cholesteryl modification.

TABLE 3

ODN sequences

| ODN | SEQ ID NO: | Sequence |
|---|---|---|
| 3Chol-2006-T4-PDE | SEQ ID NO: 3 | TCGTCGTTTTGTCGT TTTGTCGTTTTTTX |
| 2006-T4-PDE | SEQ ID NO: 3 | TCGTCGTTTTGTCGT TTTGTCGTTTTTT |

X = 3'-Cholesteryl

Figure 3:
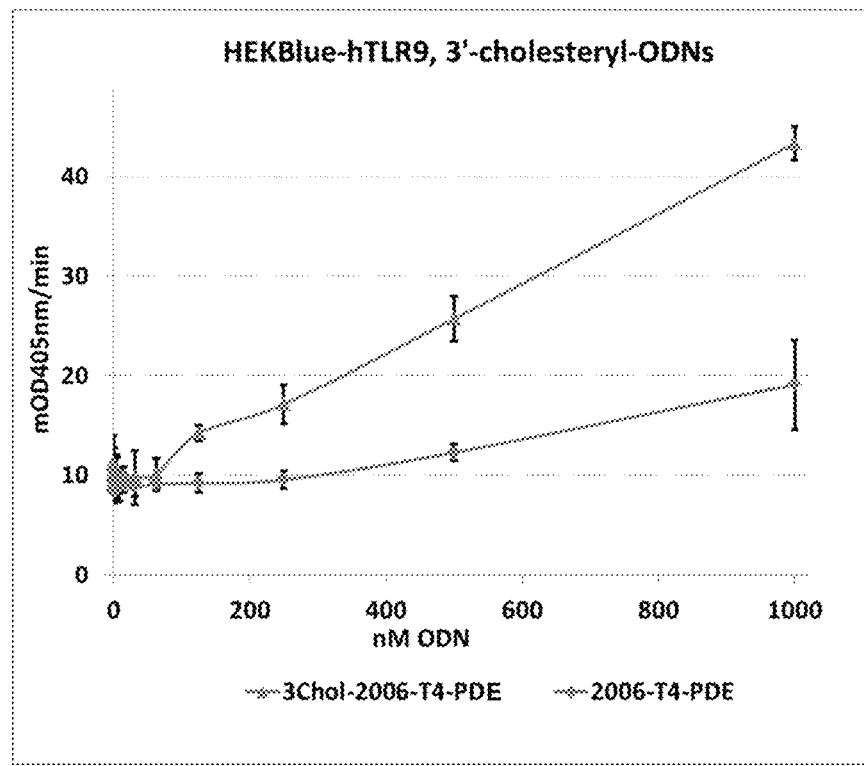
FIG. 3 depicts the ability to elicit a TLR9-mediated immune response in HEKBlue-hTLR9 cells of oligonucleotide PDE-2006 having a 3' TTTT sequence ("2006-T4-PDE") and oligonucleotide 2006-T4-PDE with a cholesteryl moiety attached via a hexanediol linker of FIG. 1 to the oligonucleotide's 3' terminus ("3Chol-2006-T4-PDE").

The results suggest that the human TLR9-stimulatory activity of 2006-T4-PDE improves considerably upon 3'-cholesteryl modification (Table 2, FIG. 3).

3'-Cholesteryl Modification of PDE-ODNs (III)

3'-cholesteryl modification (see FIG. 1 for the chemical structure of the cholesteryl-linker moiety) was applied to a PDE-ODN that has a fair activity on human TLR9, 2006-3dT4G5T4 (Table 4). The modified and unmodified forms were tested in vitro in HEKBlue-hTLR9 cells.

TABLE 4

ODN sequences

| ODN | SEQ ID NO | Sequence |
|---|---|---|
| 2006-3dT4G5T4 | SEQ ID NO: 2 | TCGTCGTTTTGTCGTTTTG TCGTTTTTTGGGGGTTTT |
| 2006-3dT4G5T43C | SEQ ID NO: 2 | TCGTCGTTTTGTCGTTTTG TCGTTTTTTGGGGGTTTTX |

X = 3'-Cholesteryl

TABLE 5

Half maximum effective concentration (EC$_{50}$) and maximum signal velocity (V$_{max}$)

| ODN | EC$_{50}$ nanomolar (nM) | Vmax milliOD 405 nm/min (mOD405/min) |
|---|---|---|
| 2006-3dT4G5T4 | 81.1 | 55 |
| 2006-3dT4G5T43C | 24.3 | 58 |

Figure 4A:
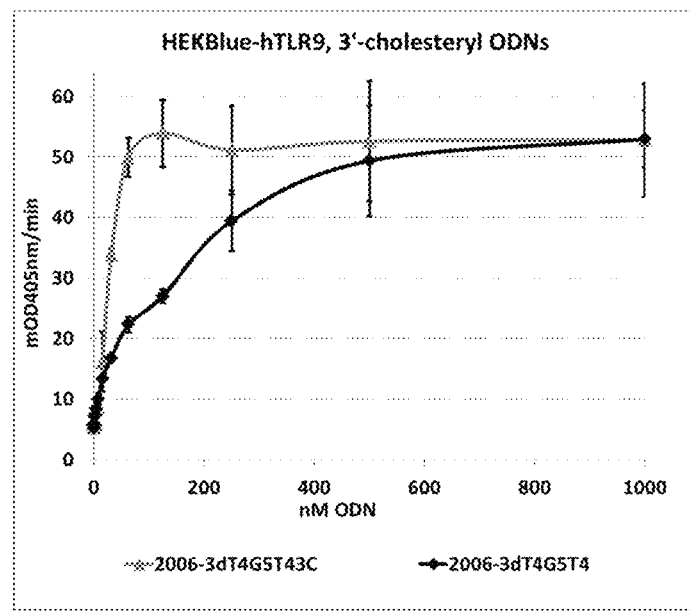
FIGS. 4A and 4B compare the TLR9 stimulatory characteristics of oligonucleotide 2006-3dT4G5T4 and oligonucleotide 2006-3dT4G5T4C.
Figure 4B:
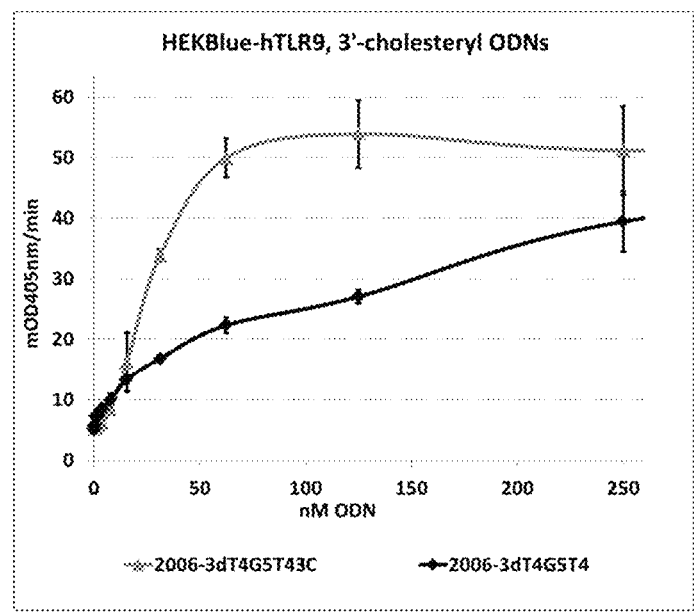

The results suggest that the TLR9-stimulatory activity of 2006-3dT4G5T4 improves considerably upon 3'-cholesteryl modification with respect to the EC$_{50}$, which is more than 3-fold lower for 2006-3dT4G5T43C (Table 5, FIGS. 4A, 4B). 3'-cholesteryl modification of PDE-ODNs (IV)

3'-cholesteryl modification (see FIG. 1 for the chemical structure of the cholesteryl-linker moiety) was applied to a PDE-ODN that has a fair activity on human TLR9, 2006-3dT4G5T4 (Table 8). The modified and unmodified forms were tested in vitro in HEKBlue-hTLR9 cells.

TABLE 8

ODN sequences

| ODN | SEQ ID NO | Sequence |
|---|---|---|
| 2006-3dT4G5T4 | SEQ ID NO: 2 | TCGTCGTTTTGTCGTTTTG TCGTTTTTTGGGGGTTTT |
| 2006-3dT4G5T43C | SEQ ID NO: 2 | TCGTCGTTTTGTCGTTTTG TCGTTTTTTGGGGGTTTTX |

X = 3'-Cholesteryl

TABLE 9

Half maximum effective concentration (EC$_{50}$) and maximum signal velocity (V$_{max}$)

| ODN | EC$_{50}$ nanomolar (nM) | Vmax milliOD 405 nm/min (mOD405/min) |
|---|---|---|
| 2006-3dT4G5T4 | 1175 | 175 |
| 2006-3dT4G5T43C | 32.0 | 56 |

Figure 5:
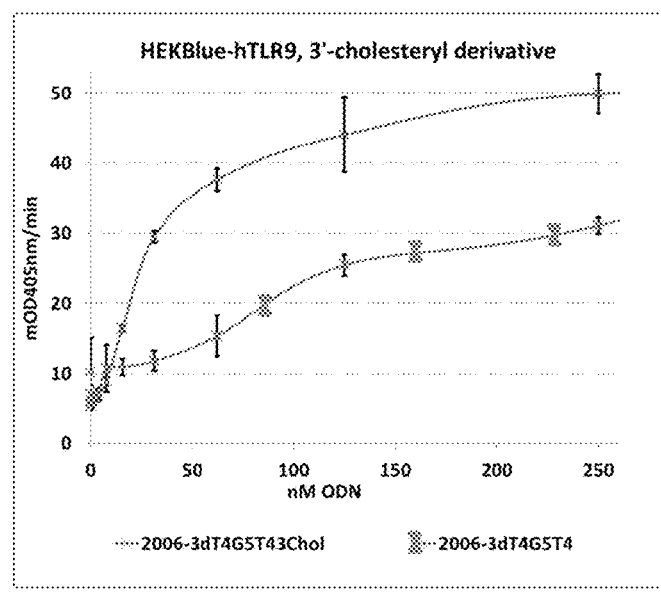
FIG. 5 compares the TLR9 stimulatory characteristics of oligonucleotide 2006-3dT4G5T4 and oligonucleotide 2006-3dT4G5T4C.

The results suggest that the TLR9-stimulatory activity of 2006-3dT4G5T4 improves considerably upon 3'-cholesteryl modification with respect to the EC$_{50}$, which is more than 36-fold lower for 2006-3dT4G5T43C (Table 9, FIG. 5).

3'-Cholesteryl Modification of PDE-ODNs (V)

3'-cholesteryl modification (see FIG. 6 for the chemical structure of the cholesteryl-linker moiety) applied to a PDE-ODN has a very poor activity on human TLR9, 2006-3dT4G5T4 (Table 10). The modified and unmodified forms were tested in vitro in HEKBlue-hTLR9 cells.

TABLE 10

ODN sequences (lower case: PTO bonds)

| ODN | SEQ ID NO: | Sequence |
|---|---|---|
| 2006-3dT4G5T4 | SEQ ID NO: 2 | TCGTCGTTTTGTCGTTTTG TCGTTTTTTGGGGGTTTT |
| 2006-3dT4G5T4-3Chol | SEQ ID NO: 2 | TCGTCGTTTTGTCGTTTTG TCGTTTTTTGGGGGTTTTX |

X = 3'-Cholesteryl

TABLE 11

Half maximum effective concentration (EC$_{50}$) and maximum signal velocity (V$_{max}$)

| ODN | EC$_{50}$ nanomolar (nM) | Vmax milliOD 405 nm/min (mOD405/min) |
|---|---|---|
| 2006-3dT4G5T4 | Poorly active | — |
| 2006-3dT4G5T4-3Chol | 68.0 | 21 |

Figure 7:
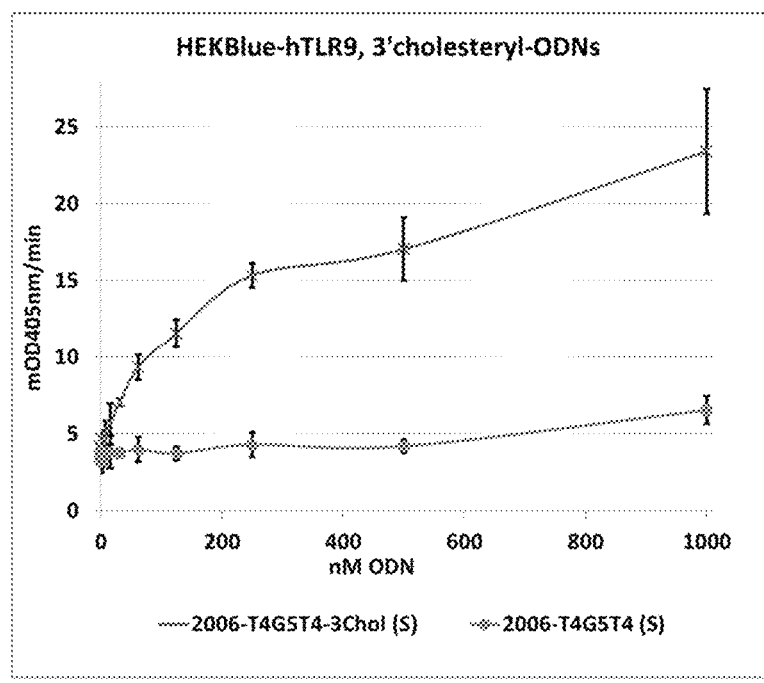
FIG. 7 compares the TLR9 stimulatory ability of oligonucleotide 2006-T4G5T4 and oligonucleotide 2006-T4G5T4 with the cholesteryl-linker moiety of FIG. 6 attached to its 3' terminus ("2006-T4G5T4-3Chol" or "2006-T4G5T4-3C").

The results suggest that the TLR9-stimulatory activity of 2006-3dT4G5T4 improves massively upon 3'-cholesteryl modification, from virtually nil to an EC$_{50}$ of 68 nM (Table 11, FIG. 7).

3'-Cholesteryl Modification of PDE-ODNs (VI)

3'-Cholesteryl Modification (See FIG. 1 for the Chemical Structure of the Cholesteryl-linker moiety) was applied to PDE-ODNs that have very poor activity or no activity on human TLR9, 2007-PDE-T4 or 2007-PDE-T4G5T4 (Table 12). The modified and unmodified forms were tested in vitro in HEKBlue-hTLR9 cells.

TABLE 12

ODN sequences

| ODN | SEQ ID NO | Sequence |
|---|---|---|
| 2007-PDE-T4 | SEQ ID NO: 4 | TCGTCGTTGTCGT TTTGTCGTTTTTT |
| 2007-PDE-T4-3Ch | SEQ ID NO: 4 | TCGTCGTTGTCGTT TTGTCGTTTTTTX |
| 2007-T4G5T4 | SEQ ID NO: 5 | TCGTCGTTGTCGTTTTGT CGTTTTTTGGGGTTTT |
| 2007-T4G5T4-3Ch | SEQ ID NO: 5 | TCGTCGTTGTCGTTTTGTC GTTTTTTGGGGTTTTX |

X = 3'-Cholesteryl

TABLE 13

Calculations of effective concentration 50% (EC$_{50}$-) and maximum signal velocity (V$_{max}$):

| ODN | EC$_{50}$ nanomolar (nM) | Vmax milliOD 405 nm/min (mOD405/min) |
|---|---|---|
| 2007-PDE-T4 | Inactive | — |
| 2007-PDE-T4-3Ch | Active | — |
| 2007-T4G5T4 | Weakly active | — |
| 2007-T4G5T4-3Ch | 24.9 | 30 |

Figure 8A:
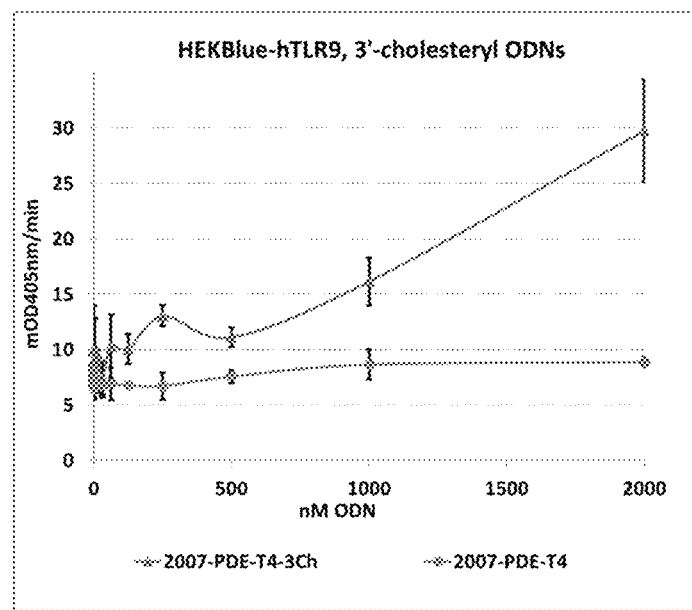
FIGS. 8A and 8B compare the immunogenicity of oligonucleotides with and without 3' cholesteryl modification.
Figure 8B:
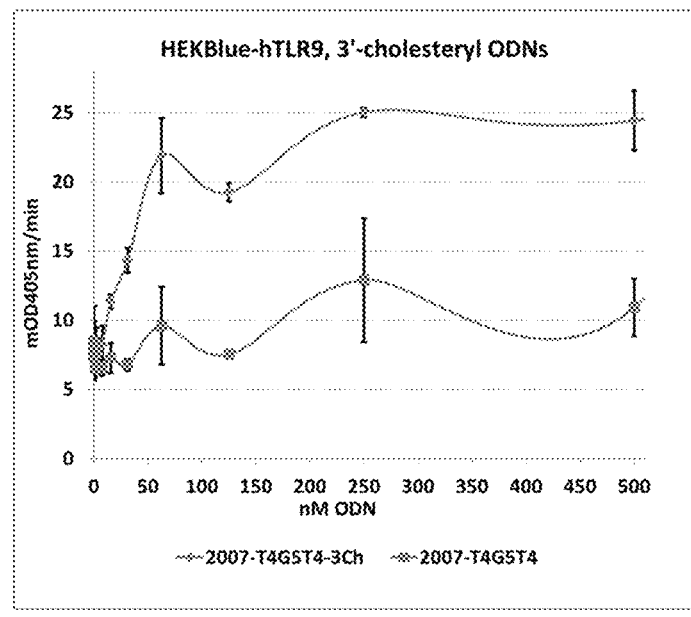

The results suggest that the TLR9-stimulatory activity of both 2007-PDE-T4 and 2007-PDE-T4G5T4 improve massively upon 3'-cholesteryl modification (FIGS. 8A and 8B), in the case 2007-T4G5T4-3Ch to an $EC_{50}$ of 24.9 nM (Table 13).

Example 2: Human TLR9, Natural Expression in Ramos-Blue Cells

3'-Cholesteryl Modification(I)

3'-cholesteryl modification (see FIG. 1 for the chemical structure of the cholesteryl-linker moiety) was applied to a PDE-ODN that has a fair activity on human TLR9, 2006-3dT4G5T4 (Table 14). The modified and unmodified forms were tested in vitro in Ramos-Blue cells. The Ramos-Blue B lymphocyte cell line (Invivogen, San Diego, Calif.) stably expresses an NF-κB/AP-1-inducible reporter gene, which allows for the detection of TLR9 signaling.

TABLE 14

| ODN sequences (lower case: PTO bonds) | | |
|---|---|---|
| ODN | SEQ ID NO | Sequence |
| 2006-3dT4G5T4 | SEQ ID NO: 2 | TCGTCGTTTTGTCGTTTTG TCGTTTTTTGGGGGTTTT |
| 2006-3dT4G5T43C | SEQ ID NO: 2 | TCGTCGTTTTGTCGTTTTG TCGTTTTTTGGGGGTTTTX |
| 2006-PTO | SEQ ID NO: 1 | tcgtcgttttgtc gttttgtcgtt |

X = 3'-Cholesteryl

TABLE 15

Half maximum effective concentration ($EC_{50}$) and maximum signal velocity ($V_{max}$)

| ODN | $EC_{50}$ nanomolar (nM) | Vmax milliOD 405 nm/min (mOD405/min) |
|---|---|---|
| 2006-3dT4G5T4 | 862 | 5.8 |
| 2006-3dT4G5T43C | 107 | 3.7 |
| 2006-PTO | 462 | 4.4 |

Figure 9A:
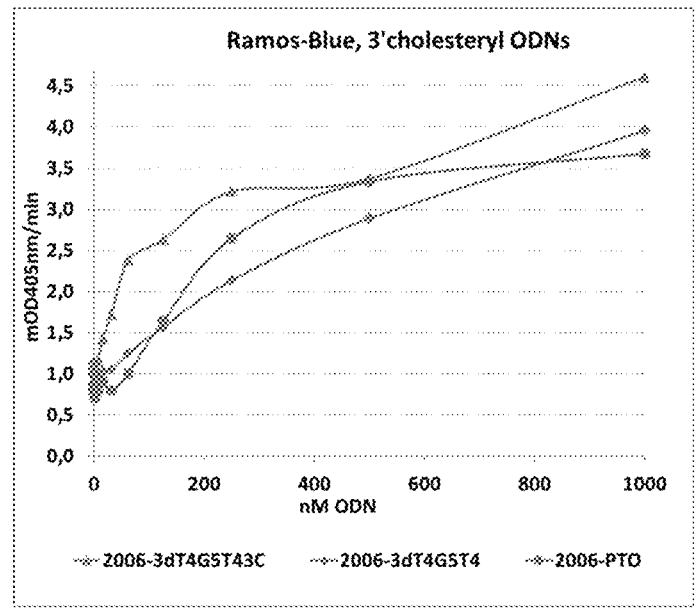
FIGS. 9A and 9B compare the immunogenicity of oligonucleotides with and without 3' cholesteryl modification. More specifically.
Figure 9B:
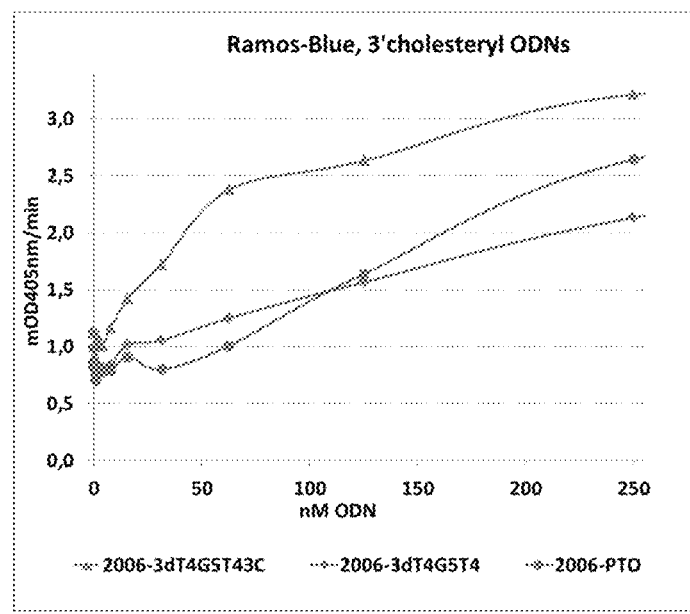

The results suggest that the TLR9-stimulatory activity of 2006-3dT4G5T4 improves considerably upon 3'-cholesteryl modification with respect to the $EC_{50}$, which is more than 8-fold lower for 2006-3dT4G5T43C (Table 15, FIGS. 9A, 9B). Also, the modified ODN 2006-3dT4G5T43C surpasses the activity of the "industry standard" ODN 2006-PTO.

3'-Cholesteryl Modification (II)

3'-cholesteryl modification (see FIG. 1 for the chemical structure of the cholestery-linker group) was applied to a PDE-ODN that has a fair activity on human TLR9, 2006-3dT4G5T4 (Table 16). The modified and unmodified forms were tested in vitro in Ramos-Blue cells.

TABLE 16

| ODN sequences | | |
|---|---|---|
| ODN | SEQ ID NO | Sequence |
| 2006-3dT4G5T4 | SEQ ID NO: 2 | TCGTCGTTTTGTCGTTTTG TCGTTTTTTGGGGGTTTT |

TABLE 16 -continued

| ODN sequences | | |
|---|---|---|
| ODN | SEQ ID NO | Sequence |
| 2006-3dT4G5T43C | SEQ ID NO: 2 | TCGTCGTTTTGTCGTTTTG TCGTTTTTTGGGGGTTTTX |

X = 3'-Cholesteryl

TABLE 17

Half maximum effective concentration ($EC_{50}$) and maximum signal velocity ($V_{max}$)

| ODN | $EC_{50}$ nanomolar (nM) | Vmax milliOD 405 nm/min (mOD405/min) |
|---|---|---|
| 2006-3dT4G5T4 | 44.3 | 6.7 |
| 2006-3dT4G5T43C | 331 | 10.7 |

Figure 10A:
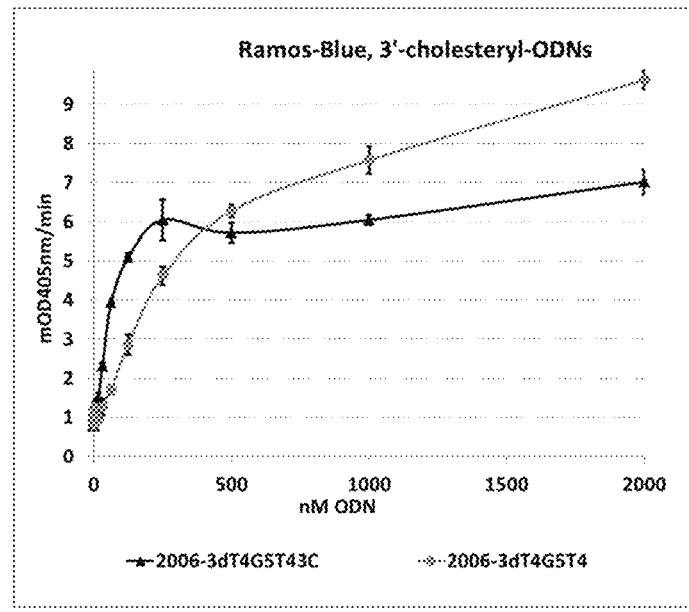
FIGS. 10A and 10B compare the ability of oligonucleotides with or without a 3' cholesteryl moiety attached via a hexanediol linker to elicit a TLR9-mediated immune response in Ramos-Blue cells. More specifically.
Figure 10B:
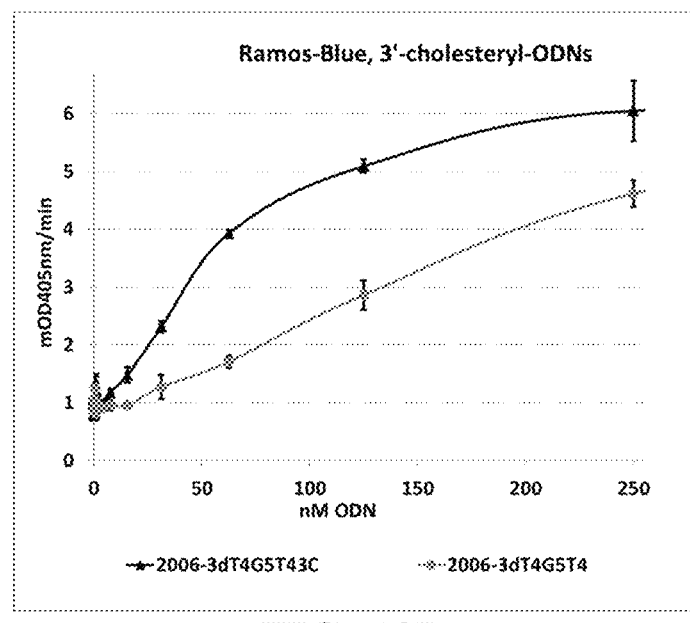

The results suggest that the TLR9-stimulatory activity of 2006-3dT4G5T4 improves considerably upon 3'-cholesteryl modification with respect to the $EC_{50}$, which is more than 7-fold lower for 2006-3dT4G5T43C (Table 17, FIGS. 10A, 10B).

3'-Cholesteryl Modification of PDE-ODNs (III)

3'-cholesteryl modification (see FIG. 1 for the chemical structure of the cholesteryl-linker moiety) was applied to a PDE-ODN that is only poorly active on human TLR9, 2006-T4-PDE (Table 18). The modified and unmodified forms were tested in vitro in Ramos-Blue cells.

TABLE 18

| ODN sequences | | |
|---|---|---|
| ODN | SEQ ID NO | Sequence |
| 3Chol-2006-T4-PDE | SEQ ID NO: 3 | TCGTCGTTTTGTCGT TTTGTCGTTTTTX |
| 2006-T4-PDE | SEQ ID NO: 3 | TCGTCGTTTTGTCGT TTTGTCGTTTTTT |

X = 3'-Cholesteryl

Figure 11:
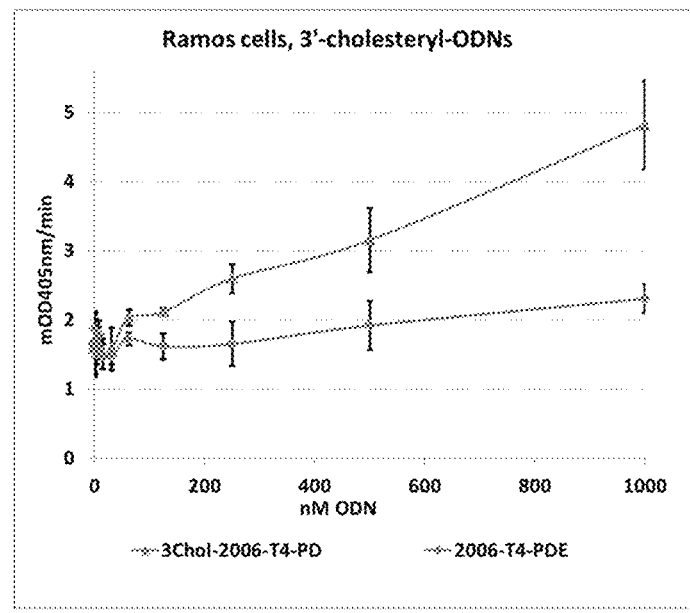
FIG. 11 compares the immunogenicity of oligonucleotide 2006-T4-PDE and oligonucleotide 2006-T4-PDE having a 3' cholesteryl moiety attached via a hexanediol linker shown in FIG. 1 ("3Chol-2006-T4-PD") in Ramos-Blue.

The results suggest that the human TLR9-stimulatory activity of 2006-T4-PDE improves considerably upon 3'-cholesteryl modification (Table 18, FIG. 11).

3'-Cholesteryl Modification of PDE-ODNs (IV)

3'-cholesteryl modification (see FIG. 6 for chemical structure of the cholesteryl-linker moiety) was applied to a PDE-ODN that has a very poor activity on human TLR9, 2006-3dT4G5T4 (Table 19). The modified and unmodified forms were tested in vitro in Ramos-Blue cells.

TABLE 19

| ODN sequences (lower case: PTO bonds) | | |
|---|---|---|
| ODN | SEQ ID NO | Sequence |
| 2006-3dT4G5T4 | SEQ ID NO: 2 | TCGTCGTTTTGTCGTTTTG TCGTTTTTTGGGGGTTTT |
| 2006-3dT4G5T4-3Chol | SEQ ID NO: 2 | TCGTCGTTTTGTCGTTTTG TCGTTTTTTGGGGGTTTTX |

X = 3'-Cholesteryl

TABLE 20

Half maximum effective concentration (EC$_{50}$)
and maximum signal velocity (V$_{max}$)

| ODN | EC$_{50}$ nanomolar (nM) | Vmax milliOD 405 nm/min (mOD405/min) |
|---|---|---|
| 2006-3dT4G5T4 | 610 | 17.2 |
| 2006-3dT4G5T4-3Chol | 46.3 | 11.9 |

Figure 12:
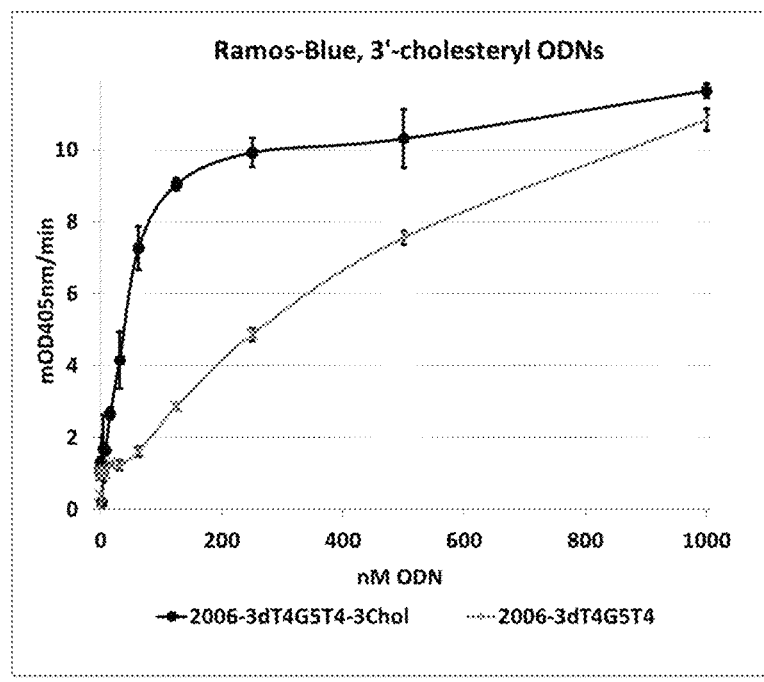
FIG. 12 compares ability to elicit a TLR9-mediated immune response in Ramos-Blue cells of oligonucleotide 2006-3dT4G5T4 and oligonucleotide 2006-3dT4G5T4-3Chol.

The results suggest that the human TLR9-stimulatory activity of 2006-3dT4G5T4 on Ramos-Blue cells improves considerably upon 3'-cholesteryl modification (Table 20, FIG. 12) by a factor of 13 with respect to EC$_{50}$.

3'-Cholesteryl Modification of PDE-ODNs (V)

3'-cholesteryl modification (see FIG. 1 for the chemical structure of the cholesteryl-linker moiety) was applied to PDE-ODNs that have very poor activity or no activity on human TLR9, 2007-PDE-T4 or 2007-PDE-T4G5T4 (Table 21). The modified and unmodified forms were tested in vitro in Ramos-Blue cells.

TABLE 21

ODN sequences

| ODN | SEQ ID NO | Sequence |
|---|---|---|
| 2007-PDE-T4 | SEQ ID NO: 4 | TCGTCGTTGTCGTTT TGTCGTTTTT |
| 2007-PDE-T4-3Ch | SEQ ID NO: 4 | TCGTCGTTGTCGTTT TGTCGTTTTTX |
| 2007-T4G5T4 | SEQ ID NO: 5 | TCGTCGTTGTCGTTTTGT CGTTTTTGGGGGTTTT |
| 2007-T4G5T4-3Ch | SEQ ID NO: 5 | TCGTCGTTGTCGTTTTGT CGTTTTTGGGGGTTTTX |
| TCG8-T4 | SEQ ID NO: 6 | TCGTCGTCGTCGTC GTCGTCGTTTT |
| TCG8-T4-3Ch | SEQ ID NO: 6 | TCGTCGTCGTCGTCGTCG TCGTCGTTTTX |

X = 3'-Cholesteryl

TABLE 22

Half maximum effective concentration (EC$_{50}$)
and maximum signal velocity (V$_{max}$)

| ODN | EC$_{50}$ nanomolar (nM) | Vmax milliOD 405 nm/min (mOD405/min) |
|---|---|---|
| 2007-PDE-T4 | — | — |
| 2007-PDE-T4-3Ch | 1219 | 17.2 |
| 2007-T4G5T4 | 401 | 22.5 |
| 2007-T4G5T4-3Ch | 28.7 | 14.1 |
| TCG8-T4 | — | — |
| TCG8-T4-3Ch | 362 | 9.7 |

Figure 13A:
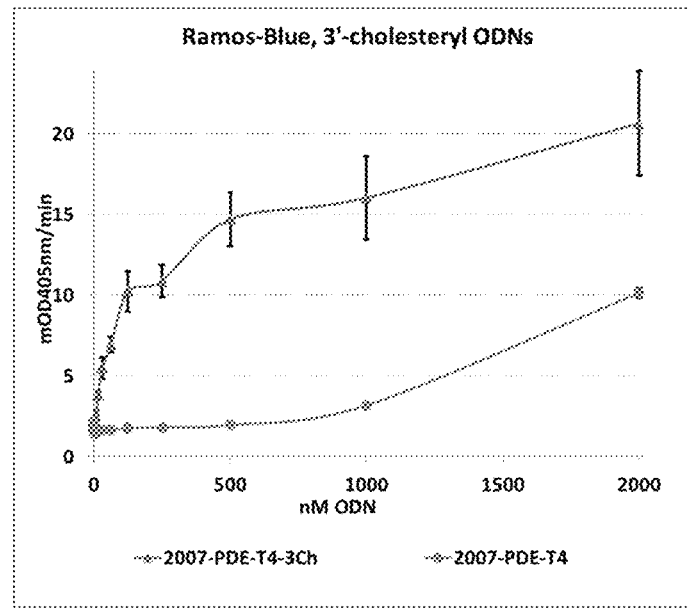
FIGS. 13A, 13B, and 13C compare the abilities of 2007-PDE-T4, 2007-T4G5T4, and TCG8-T4 oligonucleotides, with or without a cholesteryl moiety attached to the 3' terminus of the oligonucleotide, to stimulate TLR9 in Ramos-Blue cells.
Figure 13B:
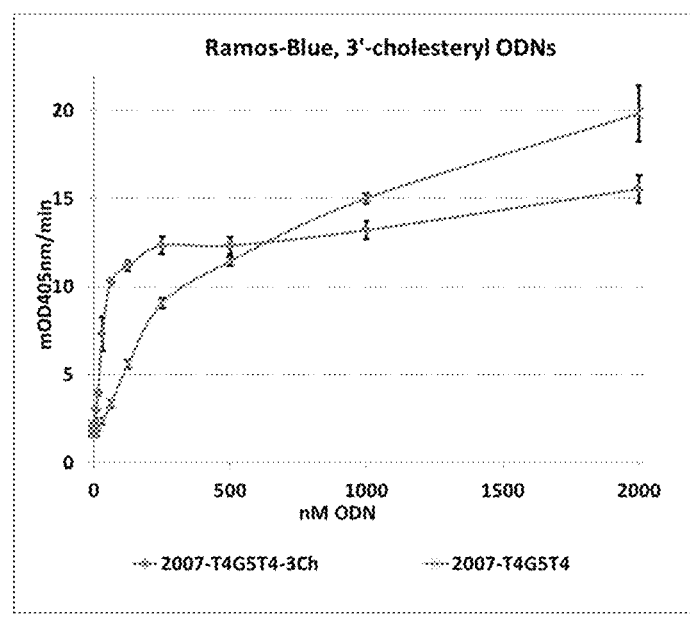
Figure 13C:
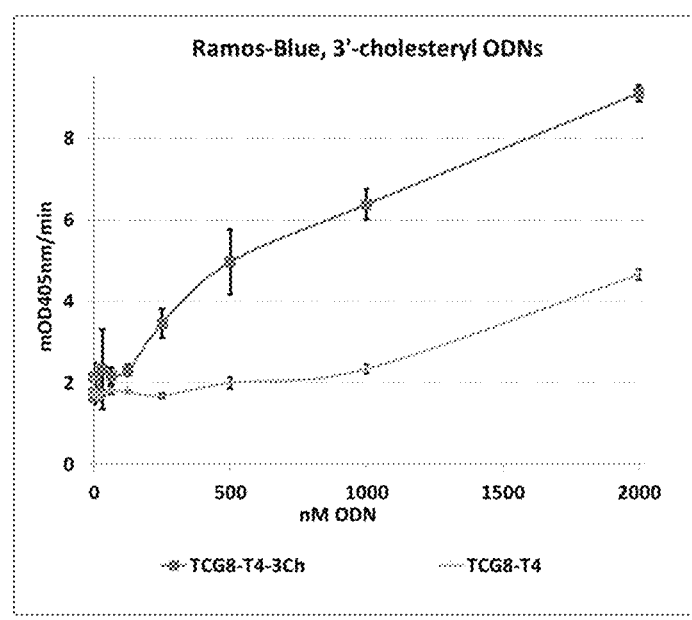

The results suggest that the human TLR9-stimulatory activity of 2006-3dT4G5T4 in Ramos-Blue cells improves considerably upon 3'-cholesteryl modification of all ODNs considered in this experiment (2007-PDE-T4, 2007-T4G5T4, TCG8-T4, Table 22, FIGS. 13A, 13B and 13C). In the case of 2007-T4G5T4-Ch, an improvement of activity by a factor of almost 14 with respect to EC$_{50}$ was noted compared to its non-modified congener.

Example 3: Mouse TLR9, Recombinant Overexpression in HEKBlue

3'-Cholesteryl Modification of PDE-ODNs

3'-cholesteryl modification (see FIG. 1 for the chemical structure of the cholesteryl-linker moiety) was applied to 2007-PDE-T4, 2007-PDE-T4G5T4, and TCG8-T4 that have a very poor activity or no activity on human TLR9 (Table 23). The modified and unmodified forms were tested in vitro in HEKBlue-mTLR9 cells (Invivogen).

TABLE 23

ODN sequences

| ODN | SEQ ID NO | Sequence |
|---|---|---|
| 2007-PDE-T4 | SEQ ID NO: 4 | TCGTCGTTGTCGT TTTGTCGTTTTTT |
| 2007-PDE-T4-3Ch | SEQ ID NO: 4 | TCGTCGTTGTCGTT TTGTCGTTTTTTX |
| 2007-T4G5T4 | SEQ ID NO: 5 | TCGTCGTTGTCGTTTTGT CGTTTTTGGGGGTTTT |
| 2007-T4G5T4-3Ch | SEQ ID NO: 5 | TCGTCGTTGTCGTTTTGT CGTTTTTGGGGGTTTTX |
| TCG8-T4 | SEQ ID NO: 6 | TCGTCGTCGTCGTC TGCGTCGTCGTTTT |
| TCG8-T4-3Ch | SEQ ID NO: 6 | TCGTCGTCGTCGTCG TCGTCGTTTTX |
| TCG8-T4G5T4 | SEQ ID NO: 8 | TCGTCGTCGTCGTCGTCGT CGTCGTTTTGGGGGTTTT |
| TCG8-T4G5T4-3Chol | SEQ ID NO: 8 | TCGTCGTCGTCGTCGTCGT CGTCGTTTTGGGGGTTTTX |

X = 3'-Cholesteryl

Figure 14A:
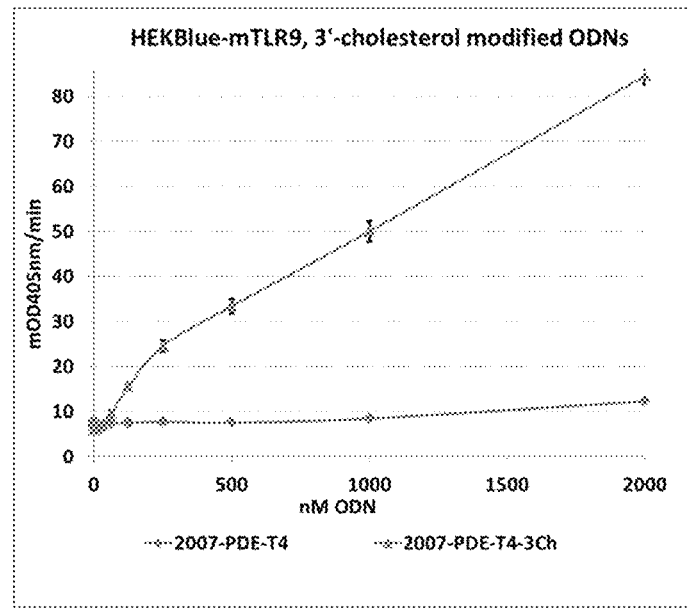
FIGS. 14A, 14B, 14C, and 14D compare stimulatory activity of several oligonucleotides and cholesteryl-modified oligonucleotides on mouse TLR9 ("mTLR9") in HEKBlue-mTLR9 cells.
Figure 14B:
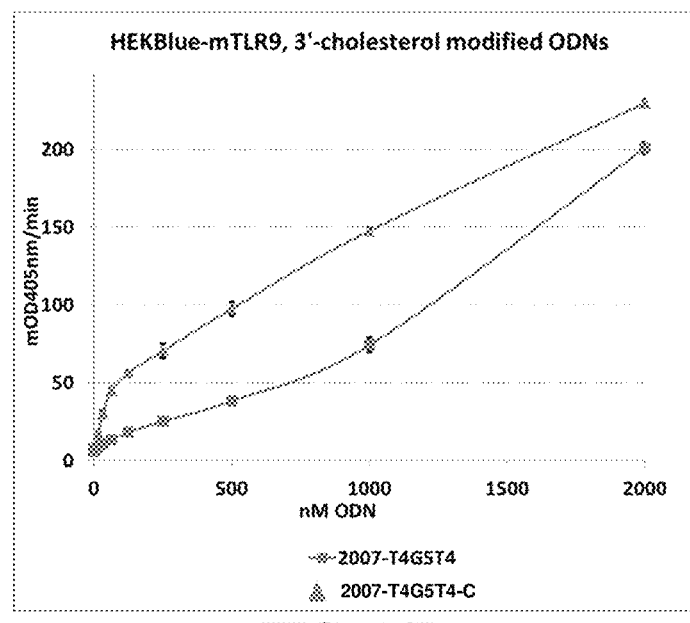
Figure 14C:
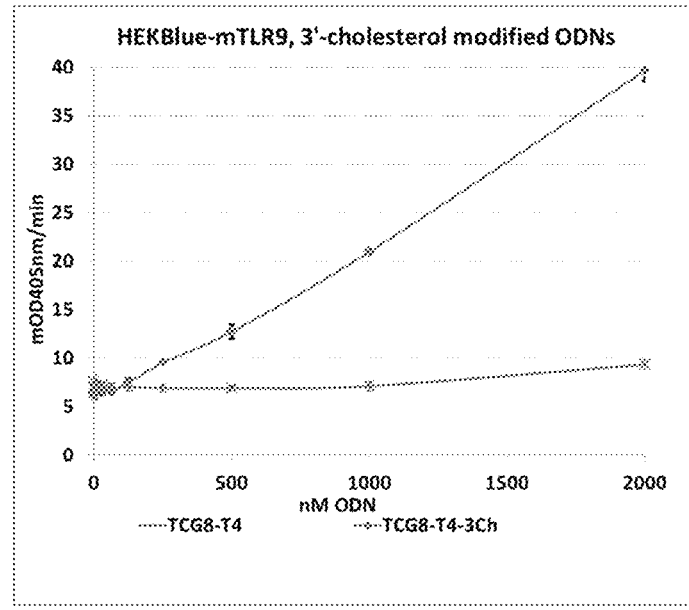
Figure 14D:
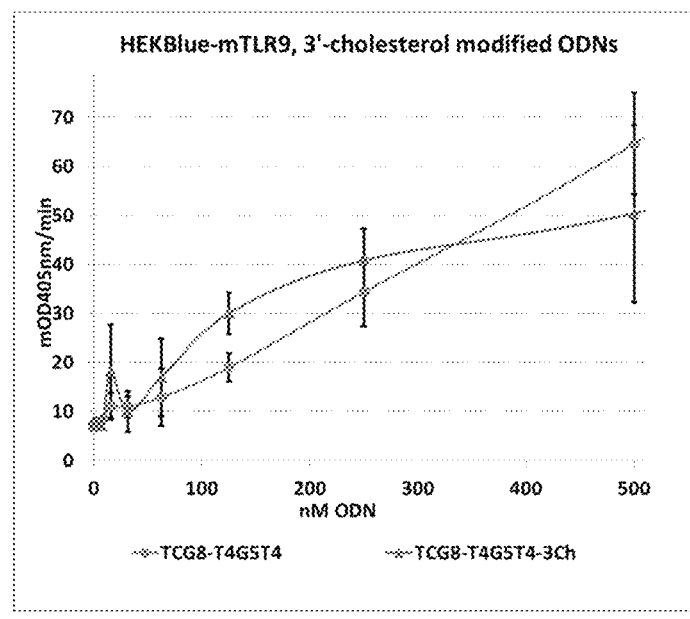

The results suggest that the mouse TLR9-stimulatory activity of all ODNs considered in this experiment (2007-PDE-T4, 2007-T4G5T4, TCG8-T4, Table 23) in HEKBlue-mTLR9 improves considerably upon 3'-cholesteryl modification in three cases (FIGS. 14A, 14B, and 14C), and marginally at low concentrations in a fourth example (FIG. 14D).

Example 4: Systematic Study on Unmodified, 3'-Cholesteryl Modified and 5'-Cholesteryl Modified ODNs on HEKBlue-hTLR9 and Ramos-Blue Cells: Structure-Activity Relationship (SAR)

HEKBlue-hTLR9

Figure 15:
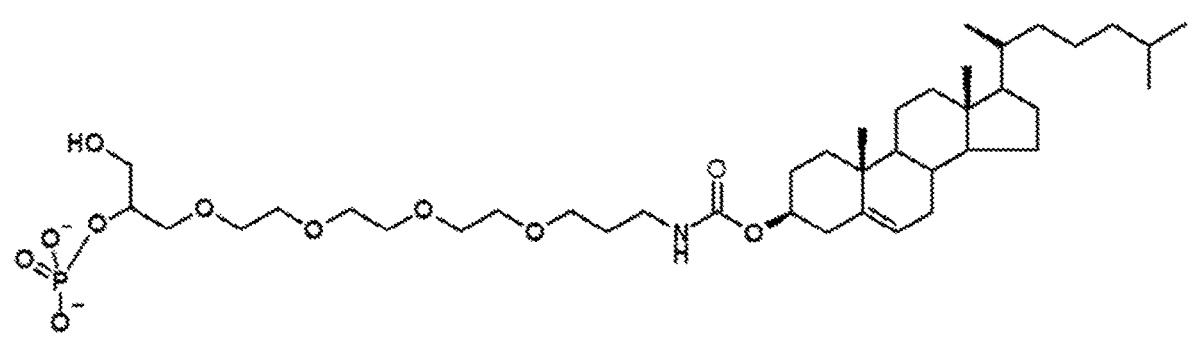
FIG. 15 depicts the chemical structure of a cholesteryl moiety attached to a hexaethylene glycol linker.
Figure 16A:
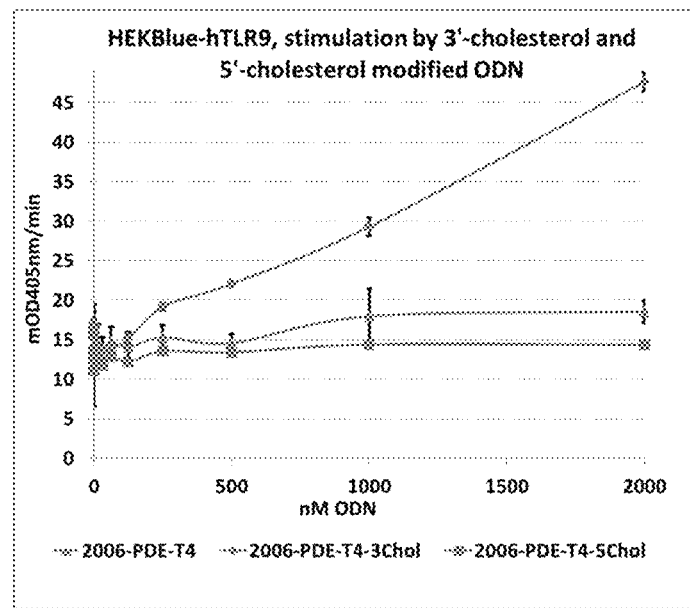
FIGS. 16A, 16B, 16C, and 16D depict the effect of modifying either the 3' or 5' termini of oligonucleotides with a cholesteryl moiety on the oligonucleotide's ability to elicit a TLR9-mediated immune response.
Figure 16B:
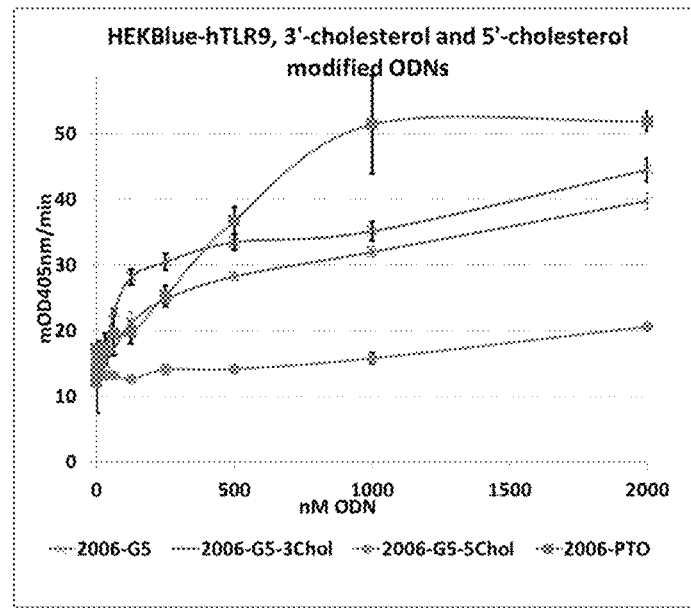
Figure 16C:
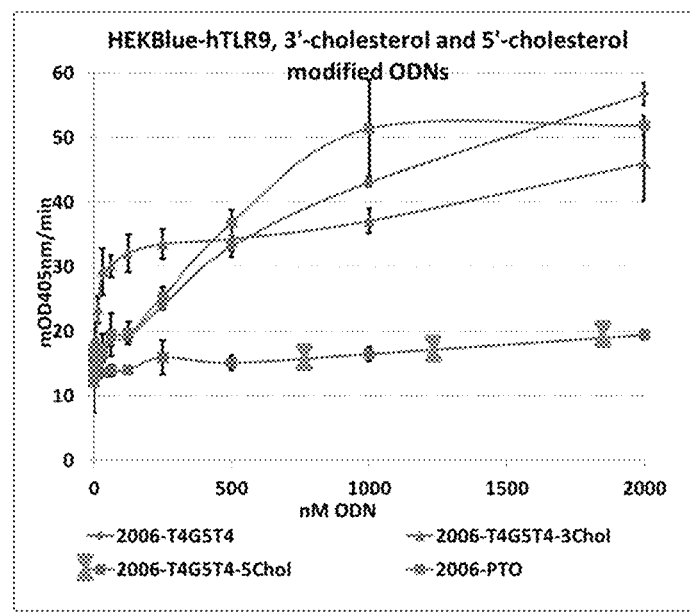
Figure 16D:
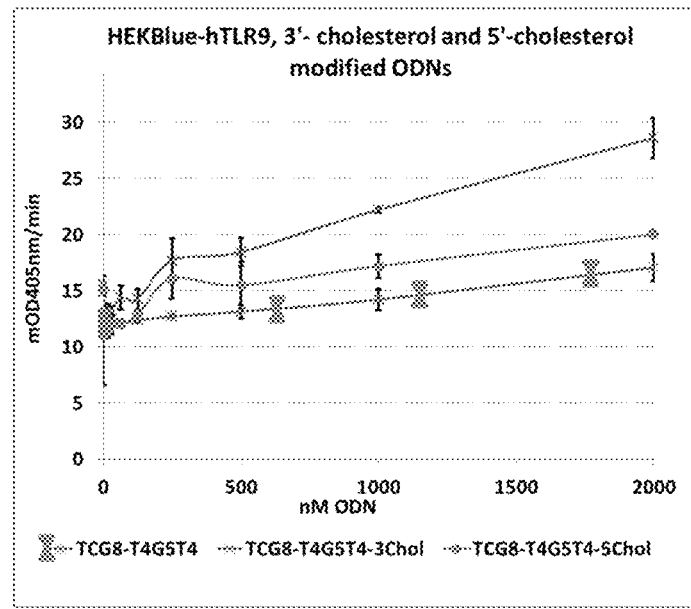

3'-cholesteryl or 5'-cholesteryl modifications (see FIGS. 6 and 15, respectively for the chemical structures of the cholesteryl-linker moieties) were applied to 4 different ODNs (Table 24). The modified and unmodified forms were tested in vitro in HEKBlue-hTLR9 cells.

TABLE 24

ODN sequences (lower case indicates PTO bonds)

| ODN | SEQ ID NO | Sequence |
|---|---|---|
| 2006-PTO | SEQ ID NO: 1 | tcgtcgttttgt cgttttgtcgtt |

TABLE 24 -continued

ODN sequences (lower case indicates PTO bonds)

| ODN | SEQ ID NO | Sequence |
|---|---|---|
| 2006-PDE-T4 | SEQ ID NO: 3 | TCGTCGTTTTGTCG TTTTGTCGTTTTTT |
| 2006-PDE-T4-3Chol | SEQ ID NO: 3 | TCGTCGTTTTGTCGT TTTGTCGTTTTTX |
| 2006-PDE-T4-5Chol | SEQ ID NO: 3 | YTCGTCGTTTTGTCG TTTTGTCGTTTTTT |
| 2006-G5 | SEQ ID NO: 7 | TCGTCGTTTTGTCGT TTTGTCGTTGGGGG |
| 2006-G5-3Chol | SEQ ID NO: 7 | TCGTCGTTTTGTCGT TTTGTCGTTGGGGGX |
| 2006-G5-5Chol | SEQ ID NO: 7 | YTCGTCGTTTTGTCG TTTTGTCGTTGGGGG |
| 2006-T4G5T4 | SEQ ID NO: 2 | TCGTCGTTTTGTCGTTTG TCGTTTTTTGGGGGTTTT |
| 2006-T4G5T4-3Chol | SEQ ID NO: 2 | TCGTCGTTTTGTCGTTTG TCGTTTTTTGGGGGTTTTX |
| 2006-T4G5T4-5Chol | SEQ ID NO: 2 | YTCGTCGTTTTGTCGTTTT GTCGTTTTTTGGGGGTTTT |
| TCG8-T4G5T4 | SEQ ID NO: 8 | TCGTCGTCGTCGTCGTCGT CGTCGTTTTGGGGGTTTT |
| TCG8-T4G5T4-3Chol | SEQ ID NO: 8 | TCGTCGTCGTCGTCGTCGT CGTCGTTTTGGGGGTTTTX |
| TCG8-T4G5T4-5Chol | SEQ ID NO: 8 | YTCGTCGTCGTCGTCGTCG TCGTCGTTTTGGGGGTTTT |

X = 3'-Cholesteryl  Y = 5'-Cholesteryl

TABLE 25

Half maximum effective concentration (EC$_{50}$) and maximum signal velocity (V$_{max}$)

| ODN | EC$_{50}$ nanomolar (nM) | Vmax milliOD 405 nm/min (mOD405/min) |
|---|---|---|
| 2006-PTO | 586 | 55 |
| 2006-PDE-T4 | Very weak | — |
| 2006-PDE-T4-3Chol | Active (linear) | — |
| 2006-PDE-T4-5Chol | Inactive | — |
| 2006-G5 | 362 | 30 |
| 2006-G5-3Chol | 144 | 30 |
| 2006-G5-5Chol | Very weak | — |
| 2006-T4G5T4 | 1133 | 69 |
| 2006-T4G5T4-3Chol | 23.3 | 26 |
| 2006-T4G5T4-5Chol | Very weak | — |
| TCG8-T4G5T4 | Weak | — |
| TCG8-T4G5T4-3Chol | Weak | — |
| TCG8-T4G5T4-5Chol | Weak | — |

In this experiment, the zero ODN values were subtracted from every data point for the EC50 and Vmax calculation, due to relatively high background readings.

For every ODN investigated in this experiment, the 3'-cholesteryl modification was most beneficial to activity on human TLR9 expressed in HEKblue cells (Table 24, FIGS. 16A, 16B, 16C, 16D). In those cases where EC$_{50}$/V$_{max}$ calculations were possible (2006-G5, 2006-T4G5T4, Table 25), it was found that the EC$_{50}$ of the unmodified ODN was lower (factors of 2.5 and 48, respectively), while 5'-cholesteryl modification led to activity loss. The EC$_{50}$s of 2006-G5-3Chol and 2006-T4G5T4-3Chol were lower than those of the "industry standard" 2006-PTO, making them candidates for immunomodulatory intervention.

Ramos-Blue

3'-cholesteryl or 5'-cholesteryl modifications (see FIGS. 6 and 15, respectively for the chemical structures of the cholesteryl-linker moietys) were applied to 4 different ODNs (Table 26). The modified and unmodified forms were tested in vitro in Ramos-Blue cells.

TABLE 26

ODN sequences (lower case: PTO bonds)

| ODN | SEQ ID NO | Sequence |
|---|---|---|
| 2006-PTO | SEQ ID NO: 1 | tcgtcgttttgt cgttttgtcgtt |
| 2006-PDE-T4 | SEQ ID NO: 3 | TCGTCGTTTTGTCG TTTTGTCGTTTTTT |
| 2006-PDE-T4-3Chol | SEQ ID NO: 3 | TCGTCGTTTTGTCG TTTTGTCGTTTTTX |
| 2006-PDE-T4-5Chol | SEQ ID NO: 3 | YTCGTCGTTTTGTCG TTTTGTCGTTTTTT |
| 2006-G5 | SEQ ID NO: 7 | TCGTCGTTTTGTCGT TTTGTCGTTGGGGG |
| 2006-G5-3Chol | SEQ ID NO: 7 | TCGTCGTTTTGTCGT TTTGTCGTTGGGGGX |
| 2006-G5-5Chol | SEQ ID NO: 7 | YTCGTCGTTTTGTCG TTTTGTCGTTGGGGG |
| 2006-T4G5T4 | SEQ ID NO: 2 | TCGTCGTTTTGTCGTTTTG TCGTTTTTTGGGGGTTTT |
| 2006-T4G5T4-3Chol | SEQ ID NO: 2 | TCGTCGTTTTGTCGTTTTG TCGTTTTTTGGGGGTTTTX |
| 2006-T4G5T4-5Chol | SEQ ID NO: 2 | YTCGTCGTTTTGTCGTTTTG TCGTTTTTTGGGGGTTTT |
| TCG8-T4G5T4 | SEQ ID NO: 8 | TCGTCGTCGTCGTCGTCGT CGTCGTTTTGGGGGTTTT |
| TCG8-T4G5T4-3Chol | SEQ ID NO: 8 | TCGTCGTCGTCGTCGTCGT CGTCGTTTTGGGGGTTTTX |
| TCG8-T4G5T4-5Chol | SEQ ID NO: 8 | YTCGTCGTCGTCGTCGTCG TCGTCGTTTTGGGGGTTTT |

X = 3'-Cholesteryl  Y = 5'-Cholesteryl

TABLE 27

Half maximum effective concentration (EC$_{50}$) and maximum signal velocity (V$_{max}$)

| ODN | EC$_{50}$ nanomolar (nM) | Vmax milliOD 405 nm/min (mOD405/min) |
|---|---|---|
| 2006-PTO | 287 | 20 |
| 2006-PDE-T4 | Weak | — |
| 2006-PDE-T4-3Chol | Active (linear) | — |
| 2006-PDE-T4-5Chol | Active (linear) | — |
| 2006-G5 | 771 | 22 |
| 2006-G5-3Chol | 247 | 14 |
| 2006-G5-5Chol | Weak | — |
| 2006-T4G5T4 | 439 | 22 |
| 2006-T4G5T4-3Chol | 42.8 | 14 |
| 2006-T4G5T4-5Chol | Weak | — |
| TCG8-T4G5T4 | Weak | — |

TABLE 27-continued

Half maximum effective concentration ($EC_{50}$)
and maximum signal velocity ($V_{max}$)

| ODN | $EC_{50}$ nanomolar (nM) | Vmax milliOD 405 nm/min (mOD405/min) |
|---|---|---|
| TCG8-T4G5T4-3Chol | 339 | 9 |
| TCG8-T4G5T4-5Chol | 1438 | 14 |

In this experiment, the zero ODN values were subtracted from every data point for the EC50 and Vmax calculation, for consistency with Table 25).

Figure 17A:
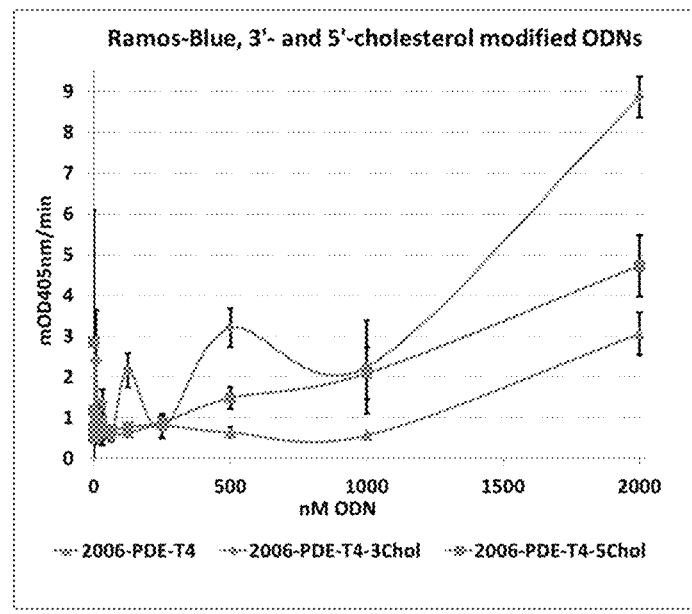
FIGS. 17A, 17B, 17C, and 17D depict the effect of modifying the 3' or 5' termini of oligonucleotides with a cholesteryl moiety.
Figure 17B:
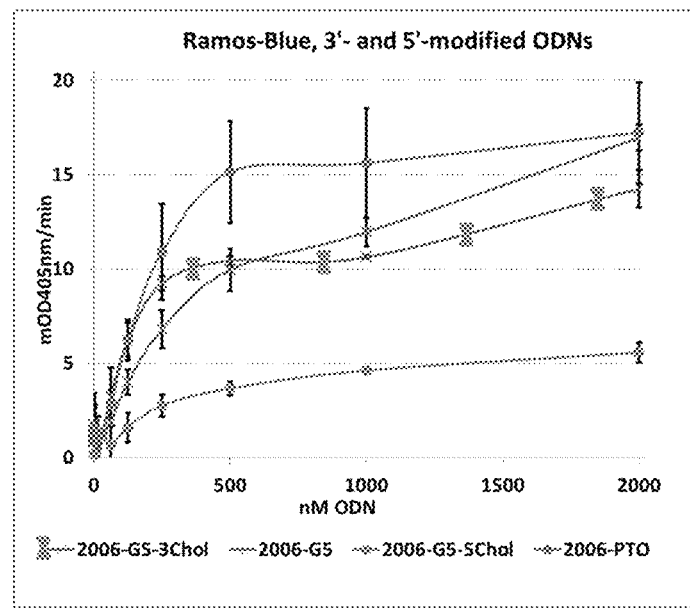
Figure 17C:
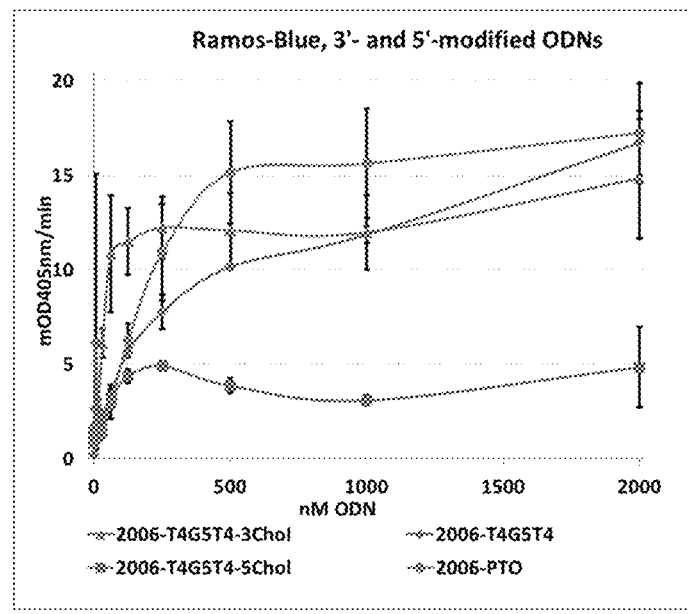
Figure 17D:
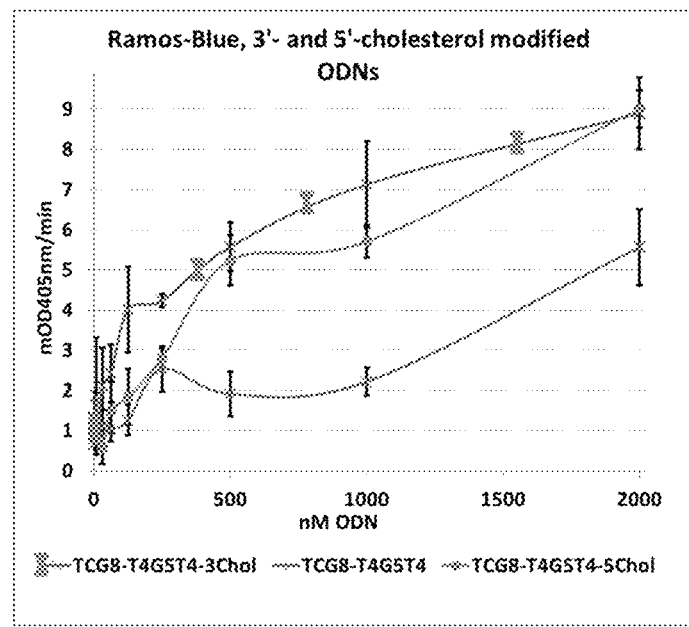

For every ODN investigated in this experiment, the 3-cholesteryl modification was most beneficial to activity on human TLR9 endogenously present in Ramos-Blue cells (Table 26, FIGS. 17A-17D). In those cases where $EC_{50}/V_{max}$ calculations were possible (2006-G5, 2006-T4G5T4, Table 25), it was found that the $EC_{50}$ of the unmodified ODN was lower (factors of 3 and 10, respectively), while 5'-cholesteryl modification led to activity loss, except for TCG8-T4G5T4, where both derivatizations led to improved activity, but more so for 3Y-cholesteryl than for 5'-cholesteryl (FIG. 17D, Table 26). The $EC_{50}$ of 2006-G5-3Chol and 2006-T4G5T4-3Chol were lower than those of the "industry standard" 2006-PTO, making them candidates for immunomodulatory intervention.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

What is claimed is:

1. An immunostimulatory oligonucleotide comprising at least one CpG motif and a 3' cholesteryl moiety,
   wherein the 3' terminal sequence of the oligonucleotide comprises a plurality of thymine nucleotides, and
   wherein the 3' terminal sequence of the oligonucleotide comprises the oligonucleotide sequence of SEQ ID NO: 9.

2. The immunostimulatory oligonucleotide of claim 1 comprising one or more phosphodiester linkages between nucleotides of the immunostimulatory oligonucleotide.

3. The immunostimulatory oligonucleotide of claim 1 comprising one or more phosphorothioate linkages between nucleotides of the immunostimulatory oligonucleotide.

4. The immunostimulatory oligonucleotide of claim 1, wherein the cholesteryl moiety is covalently attached to the 3'-terminal nucleotide of the immunostimulatory oligonucleotide via a linker.

5. The immunostimulatory oligonucleotide of claim 1, wherein the plurality of thymine nucleotides comprises consecutive thymine nucleotides.

6. The immunostimulatory oligonucleotide of claim 1, wherein the plurality of thymine nucleotides comprises between 4 and 6 consecutive thymine nucleotides.

7. The immunostimulatory oligonucleotide of claim 1, wherein the immunostimulatory oligonucleotide comprises SEQ ID NO:2, 3, 4, 5, 6, or 8.

8. The immunostimulatory oligonucleotide of claim 1, wherein the 3' terminal sequence is TTTT.

9. The immunostimulatory oligonucleotide of claim 1, wherein the 3' terminal sequence of the immunostimulatory oligonucleotide comprises a plurality of guanine nucleotides.

10. The immunostimulatory oligonucleotide of claim 9, wherein the plurality of guanine nucleotides comprises consecutive guanine nucleotides.

11. The immunostimulatory oligonucleotide of claim 9, wherein the 3' terminal sequence is GGGGG.

12. The immunostimulatory oligonucleotide of claim 9, wherein the immunostimulatory oligonucleotide comprises SEQ ID NO:7.

13. The immunostimulatory oligonucleotide of claim 1, wherein the immunostimulatory oligonucleotide comprises $(TCG)_n$, where n is between 3 and 10.

14. The immunostimulatory oligonucleotide of claim 4, wherein the linker comprises a carbon chain.

15. The immunostimulatory oligonucleotide of claim 14, wherein the carbon chain comprises between 3 and 12 carbon atoms.

16. The immunostimulatory oligonucleotide of claim 4, wherein the linker comprises a hexanediol.

17. The immunostimulatory oligonucleotide of claim 14, comprising a cholesteryl-linker moiety having the following structure:

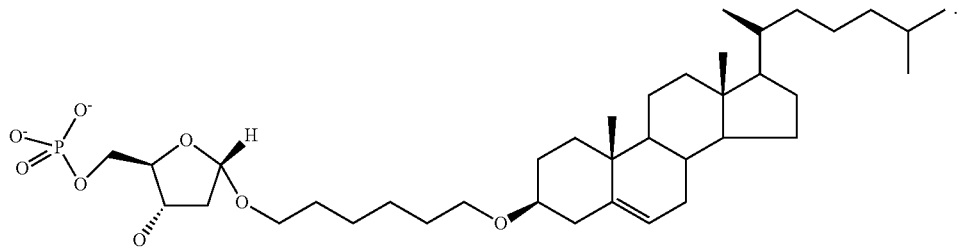

18. The immunostimulatory oligonucleotide of claim 4, wherein the linker comprises a repeated chemical unit.

19. The immunostimulatory oligonucleotide of claim 18, wherein the repeated chemical unit is repeated between 2 and 12 times.

20. The immunostimulatory oligonucleotide of claim 18, wherein the repeated chemical unit is an ethylene glycol.

21. The immunostimulatory oligonucleotide of claim 18, wherein the linker comprises a hexaethylene glycol.

22. The immunostimulatory oligonucleotide of claim 18, wherein the cholesteryl moiety is covalently bound to the linker to form a cholesteryl-linker moiety.

23. The immunostimulatory oligonucleotide of claim 22, comprising a cholesteryl-linker moiety having the following structure:

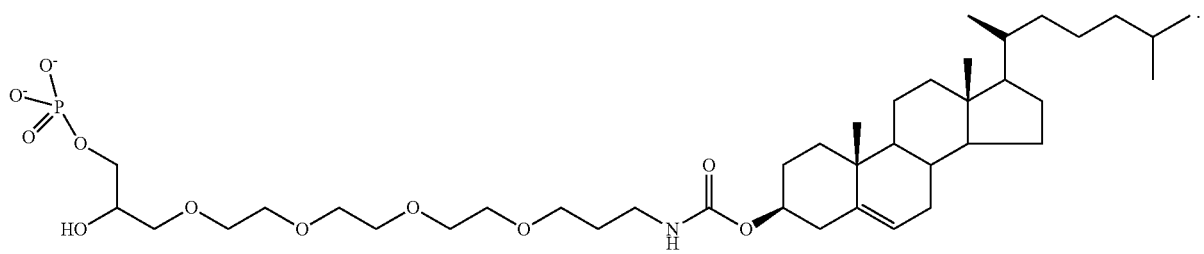

24. An immunostimulatory composition comprising the immunostimulatory oligonucleotide of claim 1.

25. The immunostimulatory composition of claim 24 further comprising a vaccine for preventing or treating an infectious disease.

26. The immunostimulatory composition of claim 24 further comprising a vector.

27. The immunostimulatory composition of claim 26, wherein the vector is a viral vector.

28. The immunostimulatory composition of claim 27, wherein the viral vector comprises the immunostimulatory oligonucleotide.

29. The immunostimulatory composition of claim 24 further comprising a pharmaceutically acceptable carrier.

30. The immunostimulatory composition of claim 29, wherein the oligonucleotide and the pharmaceutically acceptable carrier are covalently coupled.

31. The immunostimulatory composition of claim 24 further comprising a hapten.

32. The immunostimulatory composition of claim 31, wherein the oligonucleotide and the hapten are covalently coupled.

33. A method of enhancing the immunogenicity of a TLR9 ligand comprising attaching a cholesteryl moiety to the 3' terminus of the TLR9 ligand via a linker,
   wherein the TLR9 ligand is an oligonucleotide having at least one of CpG motif,
      wherein the 3' terminal sequence of the oligonucleotide comprises a plurality of thymine nucleotides, and
      wherein the 3' terminal sequence of the oligonucleotide comprises the oligonucleotide sequence of SEQ ID NO: 9.

34. The method of claim 33, wherein the cholesteryl moiety is covalently bound to the linker to form a cholesteryl-linker moiety.

35. The immunostimulatory oligonucleotide of claim 34, wherein the cholesteryl-linker moiety comprises:

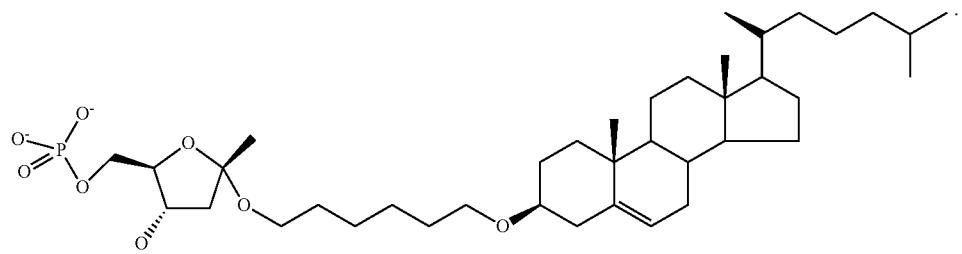

36. The immunostimulatory oligonucleotide of claim 34, wherein the cholesteryl-linker moiety comprises:

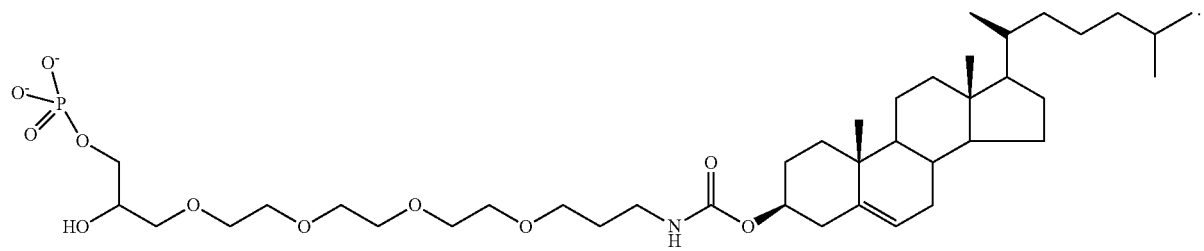

37. A method of eliciting a TLR9-mediated immune response in a subject comprising administering to the subject the immunostimulatory oligonucleotide of claim 1 or the immunostimulatory composition thereof.

38. The method of claim 37, wherein the administering is performed intravenously, intramuscularly, intramammary, intradermally, intraperitoneally, subcutaneously, by spray, by aerosol, in ovo, mucosally, transdermally, by immersion, orally, intraocularly, intratracheally, or intranasally.

39. The method of claim 37, wherein the subject is an animal.

40. The method of claim 37, wherein the subject is a mammal.

41. The method of claim 37, wherein the subject is an aquatic species.

42. The method of claim 37, wherein the subject is a mouse, pig, cow, horse, sheep, or human.

* * * * *

UNITED STATES PATENT AND TRADEMARK OFFICE
CERTIFICATE OF CORRECTION

PATENT NO. : 11,932,857 B2  
APPLICATION NO. : 16/772541  
DATED : March 19, 2024  
INVENTOR(S) : Ilg Page 1 of 1

It is certified that error appears in the above-identified patent and that said Letters Patent is hereby corrected as shown below:

On the Title Page

Item (73), change to:  
Bayer Animal Health GmbH

Signed and Sealed this  
Fourteenth Day of October, 2025

John A. Squires  
*Director of the United States Patent and Trademark Office*